United States Patent
Gaynor et al.

(10) Patent No.: US 9,851,341 B2
(45) Date of Patent: Dec. 26, 2017

(54) FIBERS WITH CHEMICAL MARKERS USED FOR CODING

(71) Applicant: Eastman Chemical Company, Kingsport, TN (US)

(72) Inventors: Scott Gregory Gaynor, Bristol, TN (US); Andrew Ervin McLeod, Jonesborough, TN (US); Michael John Rodig, Johnson City, TN (US); Jeremy Kenneth Steach, Kingsport, TN (US); Humberto Collazo, Kingsport, TN (US); Steven Anthony Wilson, Kingsport, TN (US); Lydia J. Salyer, Kingsport, TN (US); Brian Douglas Seiler, Kingsport, TN (US); Jonathan Horton, Gate City, VA (US)

(73) Assignee: Eastman Chemical Company, Kingsport, TN (US)

( * ) Notice: Subject to any disclaimer, the term of this patent is extended or adjusted under 35 U.S.C. 154(b) by 206 days.

(21) Appl. No.: 14/748,753

(22) Filed: Jun. 24, 2015

(65) Prior Publication Data

US 2015/0377854 A1 Dec. 31, 2015

Related U.S. Application Data

(60) Provisional application No. 62/018,192, filed on Jun. 27, 2014, provisional application No. 62/105,022, filed on Jan. 19, 2015.

(51) Int. Cl.
*G01N 33/36* (2006.01)
*C09K 11/88* (2006.01)
(Continued)

(52) U.S. Cl.
CPC ............... *G01N 33/36* (2013.01); *A24D 3/00* (2013.01); *A24D 3/04* (2013.01); *A24D 3/063* (2013.01);
(Continued)

(58) Field of Classification Search
CPC . A24D 3/00; A24D 3/04; A24D 3/063; D01D 5/253; D01F 1/04; D01F 1/10;
(Continued)

(56) References Cited

U.S. PATENT DOCUMENTS

| 2,208,653 A | 7/1940 | Whitehead |
| 4,280,925 A | 7/1981 | Kiefer |

(Continued)

FOREIGN PATENT DOCUMENTS

| EP | 0 066 854 A1 | 12/1982 |
| GB | 1 568 699 | 6/1980 |

(Continued)

OTHER PUBLICATIONS

Abitbol, Tiffany et al.; "Electrospinning of fluorescent fibers from CdSe/ZnS quantum dots in cellulose triacetate"; Journal of Applied Polymer Science, Wiley Online Library; 11 pages; Jan. 2010; DOI: 10.1002/APP.32782; [retrieved online Jul. 27, 2010].

(Continued)

*Primary Examiner* — David A Rogers
(74) *Attorney, Agent, or Firm* — Jennifer R. Knight; Dennis V. Carmen

(57) ABSTRACT

Disclosed are fibers which contain identification fibers. The identification fibers can comprise one or more chemical markers, or taggants, which may vary among the fibers or be incorporated throughout all of the fibers. The disclosure also relates to the method for making and characterizing the fibers. Characterization of the fibers can include identifying chemical markers and correlating the chemical markers and (Continued)

a taggant chemical marker amounts of at least one of the chemical markers to manufacturer-specific taggants to determine supply chain information. The supply chain information can be used to track the fibers from manufacturing through intermediaries, conversion to final product, and/or the consumer.

23 Claims, 10 Drawing Sheets

(51) Int. Cl.
*D01G 15/46* (2006.01)
*G01N 30/00* (2006.01)
*D01F 1/10* (2006.01)
*D01F 2/28* (2006.01)
*A24D 3/04* (2006.01)
*A24D 3/06* (2006.01)
*A24D 3/00* (2006.01)
*D06M 11/00* (2006.01)
*D06M 13/188* (2006.01)
*D06M 15/233* (2006.01)
*D06M 101/08* (2006.01)

(52) U.S. Cl.
CPC ............ *A24D 3/067* (2013.01); *C09K 11/883* (2013.01); *D01F 1/10* (2013.01); *D01F 2/28* (2013.01); *D01G 15/46* (2013.01); *G01N 30/00* (2013.01); *G01N 33/365* (2013.01); *D06M 11/00* (2013.01); *D06M 13/188* (2013.01); *D06M 15/233* (2013.01); *D06M 2101/08* (2013.01)

(58) Field of Classification Search
CPC .......... D01F 2/28; G01N 30/02; G01N 21/31; G01N 21/6428; G01N 21/73; G01N 23/00; G01N 24/087; G01N 30/72; G01N 33/36; G01N 2021/6439; G07D 7/12
See application file for complete search history.

(56) References Cited

U.S. PATENT DOCUMENTS

| | | | |
|---|---|---|---|
| 5,535,871 A | 7/1996 | Harbaugh | |
| 5,616,412 A | 4/1997 | Lin | |
| 6,036,885 A | 3/2000 | Krutak, Sr. et al. | |
| 6,214,624 B1* | 4/2001 | Barker | G01N 33/2882 436/124 |
| 6,477,227 B1 | 11/2002 | Kaiser et al. | |
| 7,546,048 B2* | 6/2009 | Schwartz | C09D 11/03 347/100 |
| 7,550,197 B2* | 6/2009 | Kittler, Jr. | A61K 9/2813 428/323 |
| 7,684,652 B2 | 3/2010 | Zorab et al. | |
| 8,124,414 B2 | 2/2012 | Harrup et al. | |
| 8,415,165 B2 | 4/2013 | Liang et al. | |
| 8,862,264 B2 | 10/2014 | Phan et al. | |
| 8,906,698 B2* | 12/2014 | Croud | G01N 21/643 250/458.1 |
| 9,266,370 B2* | 2/2016 | Jung | G07D 7/14 |
| 9,358,486 B2* | 6/2016 | McLeod | G07D 7/2033 |
| 2002/0097833 A1 | 7/2002 | Kaiser et al. | |
| 2003/0006324 A1 | 1/2003 | Pettigrew et al. | |
| 2003/0058990 A1 | 3/2003 | Kaiser et al. | |
| 2005/0227068 A1* | 10/2005 | Dugan | D01D 5/36 428/364 |
| 2007/0161115 A1* | 7/2007 | Schwartz | C09D 11/03 436/164 |
| 2007/0243234 A1 | 10/2007 | Gabriele et al. | |
| 2008/0019924 A1* | 1/2008 | Kittler | A61K 9/2813 424/10.2 |
| 2008/0293052 A1 | 11/2008 | Liang et al. | |
| 2012/0286046 A1* | 11/2012 | Ciurczak | G01J 3/0262 235/454 |
| 2012/0302474 A1* | 11/2012 | Faenza | B07C 5/342 508/296 |
| 2013/0082173 A1* | 4/2013 | Cadieux, Jr. | G01N 21/88 250/301 |
| 2013/0313484 A1 | 11/2013 | Sun | |
| 2014/0087407 A1 | 3/2014 | Deutz et al. | |
| 2015/0355091 A1* | 12/2015 | Conroy | G01N 21/643 250/459.1 |
| 2015/0379312 A1* | 12/2015 | McLeod | G01N 21/84 235/375 |

FOREIGN PATENT DOCUMENTS

| | | |
|---|---|---|
| JP | 2000 314045 A | 11/2000 |
| RU | 2 080 428 C1 | 5/1997 |
| WO | WO 98/33162 A1 | 7/1998 |
| WO | WO 00/15692 A1 | 3/2000 |
| WO | WO 02/068736 A1 | 9/2002 |
| WO | WO 2004/039913 A2 | 5/2004 |
| WO | WO 2004/094713 A2 | 11/2004 |
| WO | WO 2015/194007 A1 | 12/2015 |

OTHER PUBLICATIONS

Invitation to Pay Additional Fees and, Where Applicable, Protest Fee dated Oct. 2, 2015 received in International Application No. PCT/US2015/037595.
Invitation to Pay Additional Fees and, Where Applicable, Protest Fee dated Oct. 2, 2015 received in International Application No. PCT/US2015/037591.
Schummer, Claude et al.; "Comparison of MTBSTFA and BSTFA in derivatization reactions of polar compounds prior to GC/MS analysis"; Talanta, 77; pp. 1473-1482; 2009.
Office Communication notification dated Jun. 1, 2016 received in co-pending U.S. Appl. No. 14/748,841.
Office Communication notification dated Nov. 18, 2016 received in co-pending U.S. Appl. No. 14/748,841.
Notification of Transmittal of the International Search Report and the Written Opinion of the International Searching Authority, or the Declaration dated Jan. 18, 2016 received in International Application No. PCT/US2015/037591.
Notification of Transmittal of the International Search Report and the Written Opinion of the International Searching Authority, or the Declaration dated Jan. 18, 2016 received in International Application No. PCT/US2015/037595.
Office Communication notification dated Mar. 1, 2017 received in co-pending U.S. Appl. No. 14/748,841.
McBride, Murdoch; "Tobacco's Illicit Trade—How Legislation, Enforcement and Public Awareness are Key to Tackling Illicit Trade, Part I—Overview"; Tobacco International; pp. 17-27; Dec. 2013.
Co-pending U.S. Appl. No. 14/748,841, filed Jun. 24, 2015; Gaynor et al.

* cited by examiner

FIBERS WITH CHEMICAL MARKERS USED FOR CODING

CROSS-REFERENCES TO RELATED APPLICATIONS

This application claims priority under 35 U.S.C. 119(e) to U.S. Provisional Application No. 62/018,192, filed Jun. 27, 2014 and U.S. Provisional Application No. 62/105,022 filed Jan. 19, 2015, both of which are incorporated herein by reference in their entirety.

TECHNICAL FIELD

The disclosed embodiments relate to fibers comprising identification fibers. The identification fibers can contain a plurality of chemical markers, or taggants, which may vary among the fibers or be incorporated throughout all of the fibers. The chemical markers can be representative of specific supply chain information. The supply chain information can be used to track the fibers from manufacturing through intermediaries, conversion to final product, and/or the consumer. The disclosed embodiments also relates to the method for making and characterizing the fibers. Characterization of the fibers can include identifying chemical markers and correlating the chemical markers to manufacturer-specific taggants to determine supply chain information.

BACKGROUND

Many industries have a need to mark, tag, or identify products that allows for the tracking and tracing of products through the supply chain. One of the primary purposes for such track and trace systems is the combating of illicit trade such as counterfeiting and black market sales.

Anti-counterfeiting measures (AGMs) can be regarded as three different types: Type I (Overt), Type II (Covert) and Type III (Forensic). Type I AGMs are features incorporated into an article that are readily identified and observable to the naked eye. Examples include watermarks, color shifting inks, colored fibers, bands, or strips incorporated into the article, and holograms. Type II AGMs are features that are incorporated into the article that require some form of instrument to identify the feature in the field. The instruments required are generally those that are readily available and transportable. Some examples include the incorporation of very small text (requiring the use of a magnifying glass), UV responsive inks or threads (requiring illumination with a UV light), and barcodes or RFID tags (requiring a specialized reader). Type III AGMs are hidden attributes that require specialized laboratory equipment to identify. Some Type III examples include nano-text, micro-taggants, DNA inks, and chemical additives.

As stated above, there are many widely-used packaging and labelling taggants and anti-counterfeiting measures (AGMs) in many industries, but these more overt solutions are often susceptible to countermeasures such as destruction, modification, duplication, repackaging, or relabeling. Altering the chemical properties of the raw materials of a product can provide a more covert solution that is much more difficult to evade. These taggants may be used to track the fibers through the supply chain. The taggants may change the chemical properties of the fibers, yarn, fiber bands, and/or derivative articles in a manner that is difficult to copy or alter but is detectable using standard chemical analysis techniques.

There is a need to manufacture, test, and track fibers in yarn and/or fiber bands and their derivative articles across a wide spectrum of industries. The ability to identify the source of a yarn, fiber band, and/or an article comprising the yarn or fiber band can be achieved by embedding some form of a code in the fiber(s) during the manufacturing process that can then be later identified, retrieved, and used to identify the yarn, fiber band and/or the article. Identification tags can be incorporated into the yarn or fiber band that can denote, for example, manufacturer, manufacture site, customer, and ship-to location among other supply chain information that might be useful for the track and trace of the fiber band and/or article.

The disclosed exemplary embodiments can be used, for example, to combat the continuing and growing illicit-trade problem of tobacco products, particularly cigarettes. It has been estimated that 10-12% of all cigarette sales are illicit, either counterfeit copies or sales that avoid paying excise taxes on the cigarettes (Tobacco International, "Tackling Illicit Trade, Pt. I," December 2013). To combat this illicit trading requires a global effort consisting of manufacturers, distributors, regulators and customs/law enforcement as well as the retailer who sell the cigarettes to the consumers. There is a need to be able to track and ultimately trace components used in the construction of a cigarette. For example, the ability to track part of the supply chain path of acetate tow contained in the filter of a black market cigarette may give helpful information on the source of these illicit cigarettes.

There is a need for a traceable acetate tow that is readily manufactured, does not impact the performance of a cigarette filter, and is detectable, not only in an acetate tow band, but also in a single or a set of cigarettes/cigarette filters. There is a need for traceable acetate tow that does not impact the pressure drop and yield of a cigarette filter. There is a need for traceable acetate tow that maintains its traceability when bloomed, plasticized, and formed into a filter.

BRIEF SUMMARY

In a first embodiment, fibers comprise identification fibers, wherein the identification fibers comprise 1 to 100 chemical markers. The amount of each of the chemical markers, based on a weight of the fibers, is defined as a chemical marker amount. The chemical markers and the chemical marker amounts are representative of at least one supply chain component of the fibers.

In a second embodiment, an acetate tow band comprises fibers comprising standard fibers and identification fibers. The standard fibers comprise cellulose acetate. The identification fibers comprise 1 to 20 chemical markers. The amount of each of the chemical markers, based on a weight of the fibers, is defined as a chemical marker amount. The chemical markers and the chemical marker amounts are representative of at least one supply chain component of the acetate tow band.

In a third embodiment, a method for making an acetate tow band comprises fibers comprising standard fibers and identification fibers. The standard fibers comprise cellulose acetate. The method comprises (a) obtaining the identification fibers, wherein the identification fibers comprise 1 to 20 chemical markers; (b) producing the standard fibers on a first fiber production process; and (c) combining the standard fibers with the identification fibers into the acetate tow band. The amount of each of the chemical markers, based on a weight of the fibers, is defined as a chemical marker amount.

The chemical markers and the chemical marker amounts are representative of at least one supply chain component of the acetate tow band.

In a fourth embodiment, a method for characterizing a fiber sample comprising fibers. The fibers comprise standard fibers and identification fibers. The identification fibers comprise 1 to 100 chemical markers. The amount of each of the chemical markers, based on a weight of the fibers, is defined as a chemical marker amount. The chemical markers and the chemical marker amounts are representative of at least one supply chain component of the acetate tow band. The method comprises: (a) dissolving the fiber sample in a solvent to produce a sample solution and/or insolubles; (b) analyzing the sample solution and/or the insoluble to identify the chemical markers and each of the chemical marker amounts.

DETAILED DESCRIPTION

Figure 1A:
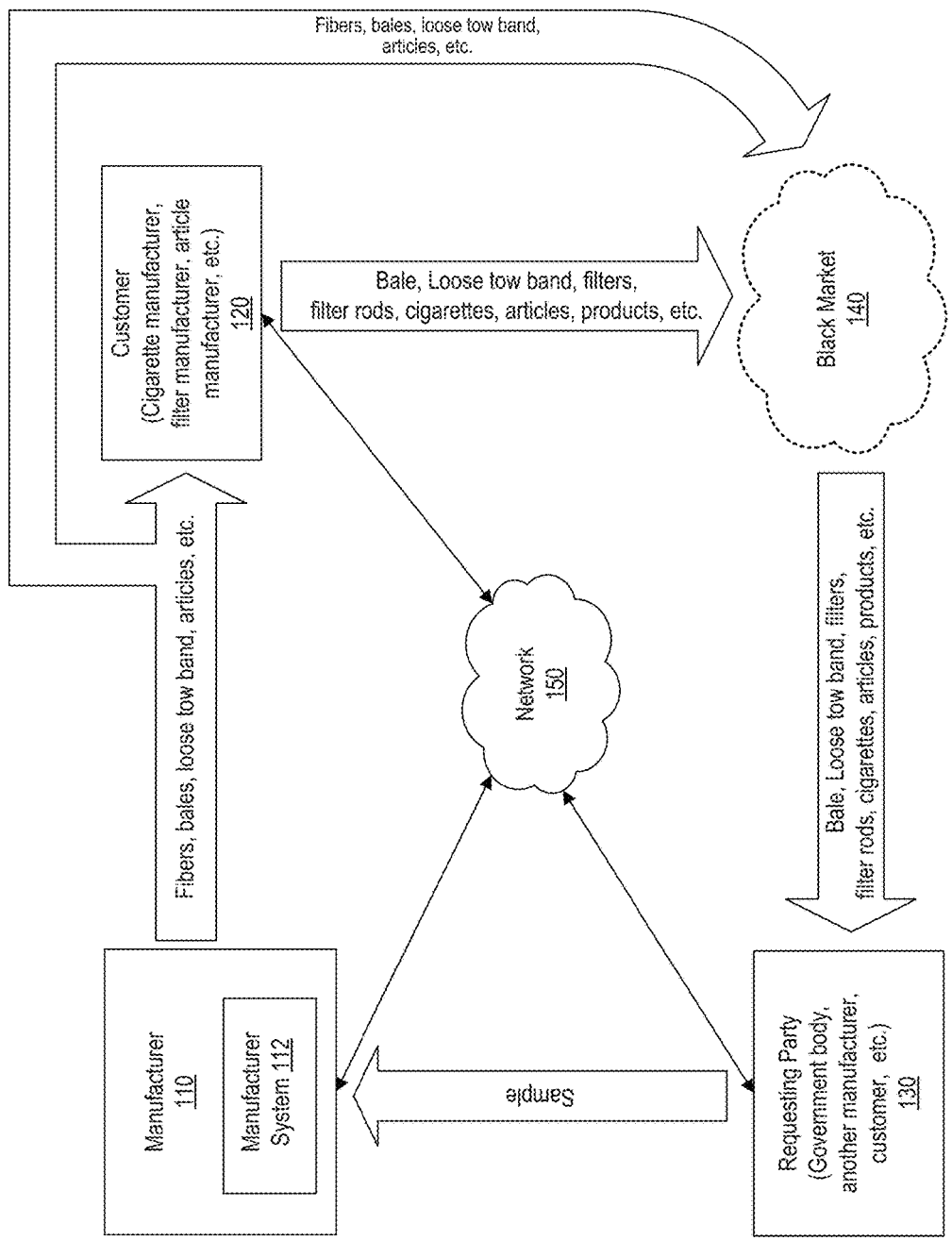
FIGS. 1A and 1B illustrates a non-limiting example of communication and shipping channels consistent with disclosed embodiments.

The disclosed embodiments provide fibers comprising identification fibers, wherein the identification fibers comprise 1 to 100 chemical markers. The amount of each of the chemical markers, based on a weight of the fibers, is defined as a chemical marker amount. The chemical markers and the chemical marker amounts are representative of at least one supply chain component of the fibers.

Unless otherwise indicated, all numbers expressing quantities of ingredients, properties such as molecular weight, reaction conditions, and so forth used in the specification and claims are to be understood as being modified in all instances by the term "about."

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "fibers", as used herein, refers to thin flexible threadlike objects. Fibers can be natural fibers or man-made. The term "polymer", as used herein refers to the base material from which the fibers are made. Non-limiting examples of polymers include acrylic, modacrylic, aramid, nylon, polyester, polypropylene, rayon, polyacrylonitrile, polyethylene, PTFE, and cellulose acetate. The term "filament", as used herein, refers to a single fiber. The term "fiber band", as used herein, refers to multiple fibers placed adjacent to each other along their lengths such that the fibers remain untwisted or entangled and form a substantially rectangular cross section with a high width-to-depth ratio. Fiber bands are often formed to allow for effective crimping of the fibers and can be cut into a staple or processed as a continuous band, depending on the end use. Fiber bands are typically not woven or knitted into a fabric article unless first converted into staple to form a thread. Fibers can also be in the form of yarn. The term "yarn", as used herein, refers to multiple fibers placed adjacent to each other along their lengths, often twisted or entangled together to improve fiber cohesiveness and performance, and typically forming a substantially rounded cross section. Yarn can be processed as continuous strands or cut into smaller lengths, depending on the end use.

Fibers can be identification fibers and/or standard fibers. The term "standard fibers", as used herein, refers to fibers which are manufactured for the primary purpose and use in producing articles. Standard fibers have not been purposefully manipulated to comprise chemical markers used to identify and track the standard fibers, yarn, a fiber band, and/or an article comprising standard fibers. The term "identification fibers", as used herein, refers to the fibers having chemical markers that can be used to identify and track the fibers, yarn, or fiber band. Identification fibers can be all of the fibers, or alternatively, identification fibers can be a subset of the fibers in the fibers, yarn, or fiber band.

The term "chemical markers", as used herein, refers to chemical compounds added to, or inherent in, the fibers for identification purposes. Non-limiting examples of chemical markers include non-volatile organic compounds, photoluminescent materials, polymeric additives, carbohydrates, metal oxides, inorganic salts, optical isomers, isotopically labeled molecules, and trace chemicals inherent to the manufacturer of the fibers and/or fiber raw materials. The term "taggant chemical markers", as used herein, refers to a collection of chemical markers used by one or more entity (e.g., manufacturer) in a system for embedding and/or determining standard fibers, yarn, and/or fiber band supply chain information.

The term "chemical marker amount", as used herein, refers to the amount of a chemical marker present in the fibers, yarn, fiber band, and/or article based on the weight of the fibers. The fibers can include identification fibers and/or standard fibers. The term of "taggant chemical marker amount", as used herein, refers to the collection of chemical marker amounts which can be used by one or more entity (e.g., manufacturer) in a system for embedding and/or determining standard fibers, yarn, fiber band, and/or article supply chain information.

The term "photoluminescent materials" as used herein, refers to either photoluminescent compounds or absorbent dyes. The concentration of the photoluminescent may be so small as to not be observed by image analysis and yet be detectable via chemical analysis, for example, spectroscopy.

The term "isotopically labeled molecules", as used herein, refers to molecules synthesized with higher levels of stable isotopes than normally found in nature. Non-limiting examples of stable isotopes include carbon ($^{12}C/^{13}C$), oxygen ($^{16}O/^{18}O$), sulfur ($^{32}S/^{34}S$) and nitrogen ($^{14}N/^{15}N$).

The term "trace chemicals inherent to the manufacture", as used herein, refers to chemical markers incorporated into a product via, for example, raw materials or processing aids. The term "trace chemicals inherent to the manufacture of polymer", as used herein, refers to chemical markers incorporated into the polymer during the polymer manufacture via, for example, raw materials or processing aids. The term "trace chemicals inherent to the manufacture of fibers", as used herein, refers to chemical markers incorporated into the fiber during the fiber manufacture via, for example, raw materials or processing aids. The term "trace chemicals inherent in the manufacture of a fiber band", as used herein, refers to chemical markers incorporated into the fiber band during the fiber band manufacture via, for example, raw materials or processing aids.

The term, "polymer", as used herein, refers to the resin or material used to make the fiber. The polymer can comprise synthetic or natural material. The term "average molecular weight", as used herein, refers to the number or weight average molecular weight of a polymer or polymeric additive. The term "spinning solvent", as used herein, refers to the material in which a polymer can be solubilized, wherein the solution of polymer and spinning solvents can be extruded into a fiber.

The term "majority of fibers", as used herein, refers to greater than 50 percent of the fibers in the yarn or fiber band based on the total number of fibers.

The term, "cellulose acetate", as used herein, refers to an acetate ester of cellulose wherein the hydrogen in the hydroxyl groups of the cellulose glucose unit is replaced by acetyl groups through an acetylation reaction. In some embodiments, suitable cellulose acetates may have a degree of substitution less than about 3 acetyl groups per glucose unite, preferably in the range of 2.2 to about 2.8, and most preferably in the range of 2.4 to 2.7.

The terms, "cellulose acetate tow" or "acetate tow", as used herein, refers to a continuous, crimped fiber band comprised of cellulose acetate fibers. The term "cellulose acetate yarn, as used herein, refers to a continuous uncrimped fiber band comprised of cellulose acetate fibers.

The term, "article", as used herein, refers to a unit produced from standard fibers, yarn, and/or a fiber band, including other components and additives needed to meet the functional requirements of the intended use. Non-limiting examples include, fabrics and other textile products, non-wovens, absorbent products, filters, filter rods, cigarette filters and liquid storage reservoirs. The term "article comprising fibers, yarn, or fiber bands", as used herein, refers to the article comprising the fibers, yarn, or fiber bands with a recognition that, in some embodiments, significant physical changes can occur to the fibers, yarn, or fiber band when it is used to make an article.

The term, "filter", as used herein refers to a semi-permeable fibrous material. Non-limiting examples of filters include a filter rod, and items made from a filter rod such as a cigarette filter. The term "filter rod", as used herein, refers to a cylindrical article, of any cross-sectional shape, produced from a fiber band and other components or additives, which can be subsequently used as a whole unit, or cut into lengths to form multiple units, for filtration of a vapor stream. Filter rods can be used to filter tobacco products, for example, traditional cigarette filters and/or other applications for other tobacco products including heat-not-burn products. Filter rods can also be used for new products comprising tobacco and other ingredients such as, for example, other plants or plant derivatives. Filter rods can be used to filter other plants and plant derivatives, with or without tobacco present. Additionally filter rods can be used to filter any vapor stream used to deliver an active ingredient such as in e-cigarette.

The term, "cigarette filter", as used herein, refers to a component of the cigarette or other smoking device which removes or decreases one or more elements from a smoke stream. The term cigarette filter is intended to encompass the filter on any smoking device including the non-limiting examples of a cigarette, a cigarette holder, a cigar, a cigar holder, a pipe, a water pipe, a hookah, an electronic smoking device, a roll-your-own cigarette, a roll-your-own cigar, cigarette filter tube, and heat-not-burn cigarettes.

The term, "supply chain information" as used herein, refers to information regarding the production of the standard fibers, yarn, and/or fiber band and information regarding the distribution of the standard fibers, yarn, and/or fiber band after its production. Supply chain information includes "supply chain components" such as, for example, manufacturer, manufacture site, manufacture line, production run, production date, package, bale, customer, customer ship-to location, warehouses, freight carrier, and/or shipment paths or routes. Supply chain components can apply to fibers, yarn, fiber bands, and/or articles.

The term, "manufacturer", as used herein, refers to the entity that produces the standard fibers, yarn, and/or fiber band.

The term "manufacture site", as used herein, refers to the geographic location or locations of the manufacturer, designated by any level of specificity including full address, continent, country, state, province, county, or city.

The term "manufacture line", as used herein, refers to specific process equipment or set of equipment used by the manufacturer to produce the standard fibers, yarn, and/or fiber band.

The term "production run", as used herein, refers to a group or set of similar or related goods that are produced by using a particular set of manufacturing procedures, processes, or conditions, and/or product specifications.

The term "customer", as used herein, refers to an entity to which the fibers, yarn, or fiber band is sold and shipped for further processing into an intermediate article or a finished product article; or an entity that purchases the yarn or fiber band for resale.

The term, "ship-to location", as used herein, refers to the geographic location of the customer designated for delivery of the fibers, yarn, or fiber band by any level of specificity including full address, continent, country, state, province, county, or city.

The term, "bale" as used herein, refers to a packaged unit of fiber bands, typically of a cubical shape, compressed to a high density, and wrapped, contained, and protected by packaging material.

The term, "warehouse" as used herein, refers to the geographical location of the warehouse designated for delivery of the fibers, yarn, or fiber band by any level of specificity including full address, continent, country, state, province, country, or city.

The term, "correlating", as used herein refers to establishing the relationship between two or more pieces of information.

The term, "manufacturer specific taggants", as used herein, refers to the particular taggants incorporated into fibers, a yarn, or a fiber band by a particular manufacturer. The term, "manufacturer specific taggant set" refers to the taggant chemical markers associated with a particular manufacturer.

The term, "fibers are produced", "producing fibers", and "fiber production process", as used herein, refers to the process steps of spinning fibers up through the gathering of the fibers into fiber bands.

The term, "identification fibers are packaged", as used herein, refers to the process steps of transferring identification fibers from the spinning machine and packaging the identification fibers, for example, onto a spool or into a bale. The identification fibers would subsequently need to be removed from the package in order to be incorporated into fibers, a yarn, or a fiber band comprising standard fibers.

The term, "spinning solution", as used herein, refers to the material to be spun. Non-limiting examples of a spinning solution can be a melt of the polymer for melt spinning or the fiber material dissolved in a solvent for dry or wet spinning.

The term, "crimper coolants", as used herein, refers to liquids applied to the fiber band at the crimper for the purpose of mitigating the heat caused by friction and/or improving processability.

The term, "chemical analysis", as used herein, refers to the equipment and techniques used to identify and/or characterize chemical substances.

Fibers, yarns, or a fiber band comprises individual fibers. The material from which the fibers are made is not particularly limiting. The fibers can comprise, for example, acrylic, modacrylic, aramid, nylon, polyester, polypropylene, rayon, polyacrylonitrile, polyethylene, PTFE, or cellulose acetate. In one aspect, the fibers comprise cellulose acetates, cellulose triacetates, cellulose propionates, cellulose butyrates, cellulose acetate-propionates, cellulose acetate-butyrates, cellulose propionate-butyrates, cellulose acetate-phthalates, starch acetates, acrylonitriles, vinyl chlorides, vinyl esters, vinyl ethers, and the like, any derivative thereof, any copolymer thereof, and any combination thereof. In one aspect, the fibers comprise cellulose acetate. In one aspect, the fibers comprise natural fibers such as, for example, cotton, hemp, and silk.

The fibers, yarn, or fiber band comprises one or more identification fibers and standard fibers. Fibers are typically produced from a polymer. In one aspect, one or more of the identification fibers comprise the same polymer as the standard fibers in the fibers, yarn, or fiber band. In another aspect, one or more of the identification fibers comprise a different material than the standard fibers in the fibers, yarn, or fiber band.

The size of the individual fibers is not particularly limiting. The size can be given in terms of effective diameter, and in one aspect, the effective diameter of the fibers range from, for example, 0.1 µm to 1000 µm, 1 µm to 500 µm, 1 µm to 100 µm, 1 µm to 30 µm, 10 µm to 1000 µm, 10 µm to 500 µm, 10 µm to 100 µm, 10 µm to 30 µm. In one aspect, the fibers comprise cellulose acetate for which size is often given in terms of denier per filament (dpf) which is defined as the weight, in grams, of a single filament 9000 meters in length. In one aspect, the size of the fibers ranges from 0.5 to 1000 dpf; 0.5 to 500 dpf; 0.5 to 100; 0.5 to 5 dpf; 0.5 to 30 dpf; 0.5 to 10 dpf; 1 to 1000 dpf; 1 to 500 dpf; 1 to 100; 1 to 5 dpf; 1 to 30 dpf; 1 to 10 dpf. In one aspect, the dpf of the fibers ranges from, for example, 1 to 30 dpf, 1 to 20 dpf, 1 to 10 dpf, 2 to 30 dpf, 2 to 20 dpf, or 2 to 10 dpf.

The number of fibers making up a fibers, yarn, or fiber band is not particularly limiting. In one aspect, the number of fibers in a yarn or fiber band may range from 10 to 50,000. In other non-limiting examples, the number of fibers in a yarn or fiber band ranges from 10 to 40,000; 10 to 30,000; 10 to 20,000; 10 to 10,000; 10 to 1000; 100 to 50,000; 100 to 40,000; 100 to 30,000; 100 to 20,000; 100 to 10,000; 100 to 1000; 200 to 50,000; 200 to 40,000; 200 to 30,000; 200 to 20,000; 200 to 10,000; 200 to 1000; 1000 to 50,000; 1000 to 40,000; 1000 to 30,000; 1000 to 20,000; 1000 to 10,000; 5000 to 50,000; 5000 to 40,000; 5000 to 30,000; 5000 to 20,000; 5000 to 10,000; 10,000 to 50,000; 10,000 to 40,000; 10,000 to 30,000; or 10,000 to 20,000.

The fibers, yarn, or fiber band comprises fibers, wherein the fibers comprise one or more identification fibers wherein the identification fibers comprise 1 to 100 chemical markers. In other aspects, the number of chemical markers ranges from 1 to 50, 1 to 20, 1 to 15, or 1 to 10, or 1 to 5, or 1 to 3.

In one aspect, essentially all of the fibers in the yarn or fiber band are identification fibers. In this aspect, the identification fibers can be distinguishable from fibers in a different yarn or fiber band. In another aspect, one or more identification fibers are distinguishable from the majority of fibers in the same yarn or fiber band. In yet another aspect, the number of identification fibers ranges from 0.001 to 100 percent of the fibers; or 0.01 to 50 percent of the fibers; or 0.01 to 25 percent of the fibers; or 0.01 to 10 percent of the fibers; or 0.01 to 5 percent of the fibers; or 0.01 to 1 percent of the fibers, each based on the total number of fibers. In another aspect, the number of identification fibers ranges from 0.01 to 100 percent of the fibers; or 1 to 100 percent of the fibers; or 25 to 100 percent of the fibers; or 50 to 100 percent of the fibers; or 30 to 80 percent of the fibers.

In one aspect, unique chemical markers are used to tag fiber products. The chemical markers can be manipulated to provide unique code. Different types of chemical markers can be applied in different amounts to increase the number of unique codes available. Additionally chemical markers can be combined with unique fiber physical structures to further increase variables for unique codes.

The identification fibers comprise chemical markers. In one aspect, the chemical markers can include non-volatile organic compounds, photoluminescent materials, polymeric additives, carbohydrates, metal oxides, inorganic salts, optical isomers, isotopically labeled molecules, and/or trace chemicals inherent to the manufacturer of the fiber band, the fibers and/or the polymer which is produced into the fibers. In one aspect, the chemical markers can include one or more taggant non-volatile organic compounds, one or more taggant photoluminescent materials, one or more taggant polymeric additives, one or more taggant carbohydrates, one or more taggant metal oxides, one or more taggant inorganic salts, one or more taggant optical isomers, one or more taggant isotopically labeled molecules, and one or more taggant trace chemicals inherent to the manufacturer of the fiber band, the fibers, and/or the polymer.

In one aspect, non-volatile organic compounds can be used as a taggant. In one aspect, one or more of the chemical markers comprise one or more taggant nonvolatile organic compounds. In one aspect the number of taggant non-volatile compounds ranges from 1 to 50, 1 to 25, 1 to 10, 1 to 5, or 1 to 3. In one aspect, the taggant nonvolatile organic compounds can comprise fatty acids. In one aspect, the taggant nonvolatile organic compounds can comprise lauric acid, palmitic acid, or stearic acid.

In one aspect, photoluminescent materials can be used as a taggant. In one aspect, one or more of the chemical markers comprise one or more taggant photoluminescent materials. In one aspect the number of taggant photoluminescent materials ranges from 1 to 50, 1 to 25, 1 to 10, 1 to 5, or 1 to 3. Non-limiting examples of photoluminescent materials include organic dyes, organometallic phosphorescent compounds, inorganic fluorescent/phosphorescent molecules, organic fluorescent molecules, inorganic quantum dots, organic quantum dots. In one aspect, the taggant photoluminescent materials comprise phosphorescent quantum dots. In one aspect, the phosphorescent quantum dots comprise Cd/Se ligand stabilized fluorescent nano-crystals.

In one aspect, polymeric additives can be used as a taggant. In one aspect, one or more chemical markers comprise one or more taggant polymeric additives. In one aspect, the number of taggant polymeric additives ranges from 1 to 50, 1 to 5, 1 to 10, 1 to 5, or 1 to 3. The taggant polymeric additives can be identified based on polymeric content and/or molecular weight. In one aspect, one or more taggant polymeric additives comprises the polymer from which the fibers are produced. In this aspect, the taggant polymeric additive is distinguishable based upon the differences in molecular weight. In one aspect, one or more taggant polymeric additives are soluble in the spinning solution. In one aspect, taggant polymeric additives comprise polystyrene with an average molecular weight ranging from 500 to 20,000,000. In other aspects, taggant polymeric additives comprise polystyrene with an average molecular weight ranging from 500 to 500,000, or 1,000 to 100,000.

In one aspect, carbohydrates can be used as a taggant. In one aspect, one or more of the chemical markers comprise one or more taggant carbohydrates. In one aspect, the number of taggant carbohydrates ranges from 50 to 1, 25 to 1, 10 to 1, 5 to 1, or 3 to 1. One or more taggant carbohydrates can comprise, for example, glucose, fructose, sucrose, and/or lactose.

In one aspect, metal oxides can be used as a taggant. In one aspect, one or more of the chemical markers comprise one or more taggant metal oxides. In one aspect, the number of taggant metal oxides ranges from 1 to 50, 1 to 25, 1 to 10, 1 to 5, or 1 to 3. One or more taggant metal oxides can comprise, for example, titanium dioxide, zirconium oxides, zinc oxides, aluminum oxides, manganese oxides, magnesium oxides, calcium oxides, tin oxides, vanadium oxides, nickel oxides and/or iron oxides. In another example, one or more taggant metal oxides can comprise titanium dioxide and/or zinc oxides.

In one aspect, inorganic salts can be used as a taggant. In one aspect, one or more chemical markers can comprise one or more taggant inorganic salts. In one aspect, the number of taggant inorganic salts ranges from 1 to 50, 1 to 25, 1 to 10, 1 to 5, or 1 to 3. Non-limiting examples of taggant inorganic salts include lithium, sodium, potassium, magnesium, and/or calcium. In one aspect, the taggant inorganic salts comprise salts of cesium, indium, or samarium.

In one aspect, optical isomers can be used as a taggant. In one aspect, one or more chemical markers can comprise one or more taggant optical isomers. In one aspect, the number of taggant optical isomers ranges from 1 to 50, 1 to 25, 1 to 10, 1 to 5, or 1 to 3.

In one aspect, isotopically labeled molecules can be used as the taggant. In one aspect, one or more chemical markers can comprise one or more taggant isotopically labeled molecules. In one aspect, the number of taggant isotopically labeled molecules ranges from 1 to 50, 1 to 25, 1 to 10, 1 to 5, or 1 to 3. One skilled in the art recognizes that, for example, $^{14}C$ or $^{18}O$ can be inserted into molecules that can be added to the polymer, the fibers, or the fiber band.

In one aspect, trace chemicals inherent to the manufacture of the fiber band, fibers, and/or polymer can be used as a taggant. In one aspect, one or more of the chemical markers comprise one or more taggant trace chemicals. In one aspect, the number of taggant trace chemicals ranges from 1 to 50, 1 to 25, 1 to 10, 1 to 5, or 1 to 3. In one aspect, one or more taggant trace chemicals are incorporated into the fibers, yarn, or fiber band through the polymer, a spinning solvent, utilities (e.g., water, plant nitrogen), and/or processing aids.

In one aspect, the amount of one or more chemical markers ranges from 1 ppb to 10,000 ppm of the fibers. In other examples, the amount of one or more chemical markers ranges from 1 ppb to 5000 ppm; 1 ppb to 1000 ppm; 1 ppb to 500 ppm; 1 ppb to 100 ppm; 1 ppb to 10 ppm; 1 ppb to 1 ppm; 1 ppb to 500 ppb; 1 ppb to 100 ppb; 10 ppb to 10,000 ppm; 10 ppb to 5000 ppm; 10 ppb to 1000 ppm; 10 ppb to 500 ppm; 10 ppb to 100 ppm; 10 ppb to 10 ppm; 10 ppb to 1 ppm; 10 ppb to 500 ppb; 10 ppb to 100 ppb; 100 ppb to 10,000 ppm; 100 ppb to 5000 ppm; 100 ppb to 1000 ppm; 100 ppb to 500 ppm; 100 ppb to 100 ppm; 100 ppb to 10 ppm; 100 ppb to 1 ppm; 100 ppb to 500 ppb; 500 ppb to 10,000 ppm; 500 ppb to 5000 ppm; 500 ppb to 1000 ppm; 500 ppb to 500 ppm; 500 ppb to 100 ppm; 500 ppb to 10 ppm; 500 ppb to 1 ppm; 1 ppm to 10,000 ppm; 1 ppm to 5000 ppm; 1 ppm to 1000 ppm; 1 ppm to 500 ppm; 1 ppm to 100 ppm; 1 ppm to 10 ppm; 10 ppm to 10,000 ppm; 10 ppm to 5000 ppm; 10 ppm to 1000 ppm; 10 ppm to 500 ppm; 10 ppm to 100 ppm; 100 ppm to 10,000 ppm; 100 ppm to 5000 ppm; 100 ppm to 1000 ppm; and/or 100 ppm to 500 ppm of the fibers.

An article can comprise the fibers, yarn, or fiber band. The article is not particularly limited. Non-limiting examples of articles comprising the fibers, yarn, or the fiber band include fabrics and other textile products, non-wovens, absorbent products, filters, filter rods, cigarette filters, liquid storage reservoirs, paper and/or currency. In one aspect, the article comprises a filter rod. In another aspect, the article comprises a cigarette filter. In one aspect, the article comprises a medical device such as a medical cloth or bandage. In another aspect, the article comprises a wicking device.

In one aspect, one or more of chemical marker amounts corresponds to a taggant chemical marker amounts. In other words, for particular chemical marker, a specific amount of chemical marker (a taggant chemical marker amount) is included in the fibers. One skilled in the art recognizes that the measured chemical marker amount and the taggant chemical marker amount may not be exactly the same due to measurement and other sources of variability. Therefore, "chemical marker amount corresponds to a taggant chemical marker amount" means that the chemical marker amount is sufficiently close to indicate the presence of the taggant chemical marker amount. The taggant chemical marker amounts for each of the chemical markers can be selected from all of the chemical marker amounts listed above. Also, the number of taggant chemical marker amounts can be the same or different for each chemical marker amount. The number of taggant chemical marker amounts is selected, in part, based upon the ability to manufacture and reliably detect discrete amounts of each of the chemical markers. In one aspect, the number of taggant chemical markers ranges from 1 to 25, 1 to 15, 1 to 10, 1 to 5, 2 to 20, 2 to 15, 2 to 10, 3 to 20, 3 to 15, 3 to 10, 4 to 20, 4 to 15, or 4 to 10.

In one aspect, the fibers, yarn, or fiber band has determinable supply chain information. The supply chain information can include manufacturer, manufacture site, manufacturing line, production run, production date, bale, warehouse, customer, and/or ship-to location. The type taggant chemical marker and/or taggant chemical marker amounts can be correlated to manufacturer-specific taggants to determine supply chain information of the fibers, yarn, fiber band, and/or article.

In one aspect, at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a yarn or fiber band comprising the standard fibers, a manufacturing site of the yarn or fiber band, a manufacturing line of the yarn or fiber band, a production run of the yarn or fiber band, a production date of the yarn or fiber band, a package of the yarn or fiber band, a warehouse of the yarn or fiber band, a customer of the yarn or fiber band, a ship-to location of the yarn or fiber band, a manufacturer of an article comprising the standard fibers, a manufacture site of the article, a manufacturing line of the article, a production run of the article, a production date of the article, a package of the article, a warehouse of the article, a customer of the article, or a ship-to location of the article.

In another aspect, the supply chain information comprises the manufacturer of the fiber band. In one aspect, the supply chain information comprises the manufacture site of the fiber band. In one aspect the supply chain information comprises the manufacturing line of the fiber band. The manufacturing line of the fiber band is the manufacturing line on which the fiber band was produced. In one aspect, the supply chain information comprises the production run of the fiber band. The production run of the fiber band is the production run within which the fiber band was produced. In one aspect, the supply chain information comprises the production date of the fiber band. The production date of the fiber band is the production date on which the fiber band was produced. In one aspect, the supply chain information comprises the bale of the fiber band. In one aspect, the supply chain information comprises the customer of the fiber band. The customer of the fiber band is the customer to whom the manufacturer plans to send or has sent the fiber band. In one aspect, the supply chain information comprises the ship-to location of the fiber band. The ship-to location of the fiber band is the specific geographic location to which the manufacturer plans to send or has sent the fiber band.

The selection of the chemical markers, taggant chemical marker amounts, number of the taggant chemical marker amounts for each of the chemical makers, and coding system can be influenced by several factors. These factors include, but are not limited to, ease of manufacturing identification fibers, yarn, and/or fiber bands comprising identification fibers; ease of detecting identification fibers, either in the fibers, yarn, the fiber band, or in an article comprising the fibers, yarn or the fiber band; impact of the identification fibers on performance characteristics of an article comprising the fibers, yarn, or the fiber band; and ease of countering the track and trace objective.

The disclosed embodiments allow for flexible implementation of a coding system for correlating the chemical markers, taggant chemical marker amounts, number of the taggant chemical marker amounts for each of the chemical makers. Described below are non-limiting examples of how coding systems can be readily implemented based upon the above described identification fibers.

In a non-limiting example of using chemical markers for a particular coding system, three chemical markers, lauric acid, palmitic acid, and stearic acid are the taggant non-volatile organic compounds. If, lauric acid can be present in the fibers in an amount of 1 wt %, 5 wt % or 10 wt %, palmitic acid can be present at 100 ppm, or 200 ppm, and stearic acid can be present at 0.5 wt %, 1 wt %, 2 wt % or 4 wt %, then there are 3 taggant lauric acid amounts, 2 taggant palmitic acid amounts, and 4 taggant stearic acid amounts. If the coding system requires each of lauric acid, palmitic acid, and stearic acid to be present, there are 48 different combinations of chemical markers and taggant chemical marker amounts. Each combination could be representative of a supply chain component.

Another non-limiting example of correlating chemical markers, taggant chemical marker amounts, number of the taggant chemical marker amounts for each of the chemical makers in a coding system includes a fiber band having identification fiber(s) with a taggant fluorescent chromophore (as the taggant photoluminescent material) having a maximum emissions wavelength ($\lambda_{max}$) obtained from the emission spectrum of the dissolved fiber band. The $\lambda_{max}$ of the taggant correlates to a number, 0-9, which is used to identify the manufacturer. The taggant fluorescent chromophore amount correlates to a number, 0-9, which is used to identify the manufacture site. Additionally, the fiber band includes identification fibers with a taggant non-volatile compound whose molecular constituents are determined and correlates to a number, 00-99, which is used to identify the customer. The taggant non-volatile compound amounts is determined and correlates to a number, 00-99, which is used to identify the ship-to location. The identity and quantity of the taggant non-volatile organic compound is determined using an analytical technique such as GC or HPLC. Such a code could be 1 3 48 39 which when compared to a database identifies the manufacturer and the manufacture site of the fiber band as well as the customer to which the fiber band is being sold, and the ship-to location. Other chemical markers may be incorporated to encode additional information.

In additional embodiments, an acetate tow band comprises fibers, comprising standard fibers and identification fibers. The standard fibers comprise cellulose acetate. The identification fibers comprise 1 to 20 chemical markers. The amount of each of the chemical markers, based on a weight of the fibers, is defined as a chemical marker amount. The chemical markers and the chemical marker amounts are representative of at least one supply chain component of the acetate tow band.

The acetate tow band of the second embodiment encompasses acetate tow bands comprising fibers with any combination of attributes described above. Specifically, the identification fiber composition, the sizes and numbers of fibers, the percentage of identification fibers in fibers, yarn, or fiber band, the chemical markers including non-volatile organic compounds, photoluminescent materials, polymeric additives, carbohydrates, metal oxides, inorganic salts, optical isomers, isotopically labeled molecules, and trace chemicals inherent to the manufacturer of the fibers and/or fiber raw materials, the chemical marker amounts, the taggant chemical marker amounts, the supply chain information, and the non-limiting coding/correlation systems apply to the acetate tow band of the second embodiment.

In one aspect, the identification fibers comprise cellulose acetate. In one aspect, the at least one supply chain component comprises the manufacturer of the acetate tow band and the customer of the acetate tow band. In one aspect, the at least one supply chain component comprises the manufacturer of the acetate tow band and the ship-to location of the acetate tow band.

The number of chemical taggants that can be used is nearly limitless. Some considerations when selecting a taggant to use in acetate tow converted to cigarette filters include being non-toxic, approved for food use (GRAS— generally regarded as safe), not providing adverse tastes or sensory changes, not interfering with the processing of the tow, and being readily analyzable using conventional laboratory methods.

Because cellulose acetate tow is made on an industrial scale, it is amenable to being tagged with various components to identify the manufacturer, as well as other supply chain information such as the customer it was sold to, location of shipment, or even a unique identifier, i.e., a serial number, for each bale of tow.

The disclosed embodiments also include a filter comprising the acetate tow band described above. In one aspect the filter comprises a filter rod or a cigarette filter.

A third disclosed embodiment provides a method for making an acetate tow band comprising fibers, comprising standard fibers and identification fibers. The standard fibers comprise cellulose acetate. The method comprises (a) obtaining the identification fibers, wherein the identification fibers comprise 1 to 20 chemical markers; (b) producing the standard fibers on a first fiber production process; and (c) combining the standard fibers with the identification fibers into the acetate tow band. The amount of each of the chemical markers, based on a weight of the fibers, is defined as a chemical marker amount. The chemical markers and the chemical marker amounts are representative of at least one supply chain component of the acetate tow band.

The method for making a yarn or fiber band, such as an acetate tow band, encompasses making a yarn or fiber band comprising the fibers with any combination of attributes disclosed above. Specifically, the identification fiber composition, the sizes and numbers of fibers, the percentage of identification fibers in fibers, yarn, or fiber band, the chemical markers including non-volatile organic compounds, photoluminescent materials. polymeric additives, carbohydrates, metal oxides, inorganic salts, optical isomers, isotopically labeled molecules, and trace chemicals inherent to the manufacturer of the fibers and/or fiber raw materials, the chemical marker amounts, the taggant chemical marker amounts, the supply chain information, and the non-limiting coding/correlation systems apply to the acetate tow band of the second embodiment given above apply equally well to the method for making a fiber band.

In one aspect, at least a portion of the standard fibers are produced on a fiber production process. In another aspect, standard fibers are received from a third party. Obtaining the identification fibers comprises at least one of (i) producing at least a portion of the identification fibers on the standard fibers' fiber production process, (ii) producing at least a portion of the identification fibers on a process distinct from the standard fibers' fiber production process, or (iii) receiving at least a portion of the identification fibers from a third party.

In one aspect, the identification fibers are coproduced with the standard fibers and all of the fibers making up a yarn or fiber band are combined directly downstream of the fiber production process.

In another aspect, the identification fibers are produced and packaged separately from standard fibers and the identification fibers are combined with the standard fibers to produce a fiber band. The standard fibers may also have been packaged before combining with the identification fibers, or the identification fibers may be combined with the standard fibers before packaging of the fiber band.

The spinning process used for producing the fibers is not particularly limited. In one aspect, the fibers are produced using dry spinning, solution spinning, melt spinning, electro spinning, gel spinning, multi-component spinning, melt blowing, and/or solution blowing. In another aspect, the fibers are produced using dry spinning, solution spinning, melt spinning, electro spinning, gel spinning, and/or multi-component spinning. In a further aspect, the fibers comprise cellulose acetate and are produced using dry spinning.

In one aspect, one or more chemical markers are selected from the group consisting of one or more taggant non-volatile organic compounds, one or more taggant photoluminescent materials, one or more taggant polymeric additives, one or more taggant carbohydrates, one or more taggant metal oxides, one or more taggant inorganic salts, one or more taggant optical isomers, one or more taggant isotopically labeled molecules and one or more taggant trace chemicals inherent to the manufacturer of said fiber band, said fibers and/or said polymer.

In one aspect, the amount of one or more chemical markers (i.e. chemical marker amounts) ranges from 1 ppb to 10,000 ppm; 1 ppb to 5000 ppm; 1 ppb to 1000 ppm; 1 ppb to 500 ppm; 1 ppb to 100 ppm; 1 ppb to 10 ppm; 1 ppb to 1 ppm; 1 ppb to 500 ppb; 1 ppb to 100 ppb; 10 ppb to 10,000 ppm; 10 ppb to 5000 ppm; 10 ppb to 1000 ppm; 10 ppb to 500 ppm; 10 ppb to 100 ppm; 10 ppb to 10 ppm; 10 ppb to 1 ppm; 10 ppb to 500 ppb; 10 ppb to 100 ppb; 100 ppb to 10,000 ppm; 100 ppb to 5000 ppm; 100 ppb to 1000 ppm; 100 ppb to 500 ppm; 100 ppb to 100 ppm; 100 ppb to 10 ppm; 100 ppb to 1 ppm; 100 ppb to 500 ppb; 500 ppb to 10,000 ppm; 500 ppb to 5000 ppm; 500 ppb to 1000 ppm; 500 ppb to 500 ppm; 500 ppb to 100 ppm; 500 ppb to 10 ppm; 500 ppb to 1 ppm; 1 ppm to 10,000 ppm; 1 ppm to 5000 ppm; 1 ppm to 1000 ppm; 1 ppm to 500 ppm; 1 ppm to 100 ppm; 1 ppm to 10 ppm; 10 ppm to 10,000 ppm; 10 ppm to 5000 ppm; 10 ppm to 1000 ppm; 10 ppm to 500 ppm; 10 ppm to 100 ppm; 100 ppm to 10,000 ppm; 100 ppm to 5000 ppm; 100 ppm to 1000 ppm; and/or 100 ppm to 500 ppm of said fibers.

The method for incorporating the chemical markers into the fiber band is not particularly limited. Chemical markers disclosed herein can be incorporated in the cellulose acetate tow manufacturing process by several possible methods and at many steps or locations in the process. The general methods would include introduction and mixing in bulk while the product or its raw materials are in a liquid form (e.g. pigment slurry; acid dope; acetone dope; acetic acid; acetic anhydride; neutralization agents; lubricant emulsion) or applied to the surface of the product when in solid form (e.g. pulp rolls; pigment granules; cellulose acetate flake; tow after spinning).

In one aspect, one or more chemical markers can be added to the polymer from which the identification fibers are made. In one aspect, the chemical marker is added to the spinning solution. The spinning solution is subsequently spun into one or more identification fibers. The chemical marker can be added to the spinning solution upstream of the manufacturing line to be incorporated into all of the fibers of the fiber band or upstream of one or more spinning cabinets or one or more individual spinnerets to incorporate the marker into a portion of the fibers of the fiber band. Static mixers can be used to mix the chemical marker in the spinning solution piping without mechanical agitation. The addition of the chemical markers at the cabinet or spinneret level allows for quicker and less costly purging of the spinning system when chemical marker changes are needed to represent a different supply chain component, for example a different ship to location. In one aspect, one or more of the chemical markers is added to a spinning solution upstream of the first fiber production process, at a spinning cabinet contained within the first fiber production process, or at an individual spinneret contained within the spinning cabinet.

In one aspect, chemical markers are applied to one or more identification fibers by surface application at any point before, during, and/or after the forming of the yarn or fiber band; before, during and/or after the crimping of the fiber band; before, during and/or after the conditioning of the yarn or fiber band; before, during and/or after the conveyance of the yarn or fiber band to the packaging process. In one aspect, the spin finish comprises one or more chemical markers and is applied to the fiber through existing spin finish application equipment. In another aspect, the existing crimper coolant comprises one or more chemical markers.

In one aspect chemical markers can be applied by surface application to one or more identification fibers by a method selected from the group consisting of dipping, immersing, submerging, soaking, rinsing, washing, painting, coating, showering, drizzling, spraying (as liquid or atomized), placing, dusting, sprinkling, affixing, pouring, and direct metering.

In addition to the flexibility of where and how chemical markers are added to the process for making a yarn or fiber band, the form of the chemical markers is not particularly limited. In one aspect, chemical markers can be applied in a form selected from the group consisting of neat, in a solution, in an emulsion, and in a suspension.

The location at which the chemical markers are added may determine the degree of differentiation possible within the supply chain information, e.g. manufacturing location, manufacturing line, production run, or bale. Generally the further upstream the chemical markers are incorporated, the less differentiation is possible. However, the further downstream the chemical markers are applied, the greater the potential capital expense and manufacturing complexity due to the need for a multiplicity of equipment additions and modifications. In one aspect, one or more chemical markers can be added at the point of manufacture of the article. In one aspect, one or more chemical markers can be added at the plugmaker when an acetate tow band is converted into a filter rod.

In one aspect, the identification fibers comprise cellulose acetate. In one aspect, the at least one supply chain component comprises the manufacturer of the acetate tow band and the customer of the acetate tow band. In one aspect, the at least one supply chain component comprises the manufacturer of the acetate tow band and the ship-to location of the acetate tow band.

The disclosed embodiments also provide a method for characterizing a fiber sample comprising fibers. The fibers comprise standard fibers and identification fibers. The identification fibers comprise 1 to 100 chemical markers. The amount of each of the chemical markers, based on a weight of the fibers, is defined as a chemical marker amount. The chemical markers and the chemical marker amounts are representative of at least one supply chain component of the acetate tow band. The method comprises: (a) dissolving the fiber sample in a solvent to produce a sample solution and/or insolubles; (b) analyzing the sample solution and/or the insoluble to identify the chemical markers and the chemical marker amounts.

The method for characterizing a fiber sample encompasses characterizing a fiber sample comprising fibers, a yarn, fiber band, and/or article comprising the fibers with any combination of attributes disclosed above. Specifically, the identification fiber composition, the sizes and numbers of fibers, the percentage of identification fibers in a fibers, yarn, or fiber band, the chemical markers including non-volatile organic compounds, photoluminescent materials, polymeric additives, carbohydrates, metal oxides, inorganic salts, optical isomers, isotopically labeled molecules, and trace chemicals inherent to the manufacturer of the fibers and/or fiber raw materials, the chemical marker amounts, the taggant chemical marker amounts, the supply chain information, and the non-limiting coding/correlation systems apply to the method for characterizing a fiber sample. Additionally, the fiber band can be made using any combination of attributes disclosed above in the method for making a fiber band.

In one aspect, the solvent is selected from the group consisting of ethers; ketones; aliphatic and aromatic hydrocarbons; water; and ionic liquids. In one aspect, the aliphatic and aromatic hydrocarbons comprise hetero atoms, wherein the heteroatoms comprise halogens, amines, oxygen, sulfur and/or phosphorus. In another aspect, the solvent comprises acetone, tetrahydrofuran, dichloromethane, methanol, chloroform, dioxane, N,N-dimethylformamide, dimethyl sulfoxide, methyl acetate, ethyl acetate, nitric acid and/or pyridine.

The equipment and techniques used to identify the chemical markers are not particularly limited. One skilled in the art of analytical chemistry will recognize that there are several chemical analysis technologies useful in analyzing articles and/or prepared samples, for example, by dissolving the articles in a solvent. In one aspect, the chemical markers are analyzed using mass spectrometry, spectroscopy, nuclear magnetic resonance, and/or x-ray diffraction. In one aspect, the chemical markers are analyzed using chromatography and/or inductively coupled plasma. One skilled in the art recognizes that these are broad categories of chemical analysis technologies. The specific types of each chemical analysis technology can be used in analyzing chemical markers in the fiber band.

In one aspect, the method for characterizing the fiber sample further comprises (a) correlating one or more of chemical markers and/or chemical marker amounts to a database comprising manufacturer-specific taggants; and (b) determining supply chain information of the fiber sample. The supply chain information can include manufacturer, manufacture site, manufacturing line, production run, production date, bale, warehouse, customer, and/or ship-to location.

In one aspect, the supply chain information comprises the manufacturer of the fiber band in the article. In one aspect, the supply chain information comprises the manufacture site of the fiber band in the article. In one aspect the supply chain information comprises the manufacturing line of the fiber band in the article. The manufacturing line of the fiber band is the manufacturing line on which the fiber band was produced. In one aspect, the supply chain information comprises the production run of the fiber band in the article. The production run of the fiber band is the production run within which the fiber band was produced. In one aspect, the supply chain information comprises the production date of the fiber band in the article. The production date of the fiber band is the production date on which the fiber band was produced.

In one aspect, the supply chain information comprises the bale of the fiber band in the article. In one aspect, the supply chain information comprises the customer of the fiber band in the article. The customer of the fiber band is the customer to whom the manufacturer plans to send or has sent the fiber band. In one aspect, the supply chain information comprises the ship-to location of the fiber band in the article. The ship-to location of the fiber band is the specific geographic location to which the manufacturer plans to send or has sent the fiber band.

The disclosed embodiments also include the making an article with a fiber band having any of the disclosed features. Additional disclosed embodiments also include an article comprising a fiber band having any of the disclosed features. In other embodiments, the fibers having any of the disclosed features are formed into a yarn.

In further embodiments, a method for embedding supply chain information into fibers includes obtaining standard fibers and obtaining identification fibers. In one aspect, the identification fibers may include one or more chemical markers, and each of the chemical markers may be present within the identification fibers in a corresponding chemical marker amount. In further aspects, at least one of the chemical marker amounts may represent a taggant chemical marker amount. The method may also include combining the standard fibers with the identification fibers. In certain aspects, the one or more chemical markers and/or the at least one taggant chemical marker amount may be representative of at least one component of a supply chain.

In some aspects, at least a portion of the standard fibers, and additionally or alternatively, at least a portion of the identification fibers, may include cellulose acetate fibers. For example, the standard fibers may be combined with the identification fibers to form a cellulose acetate tow band. Further, in some instances, a portion of at least one of a filter rod or cigarette filter may be formed from the cellulose acetate tow band. In other aspects, the standard fibers may be combined with the identification fibers to form a portion of at least one of fabrics, other textile products, non-wovens, and/or absorbent products.

The at least one supply chain component may include a manufacturer, a manufacture site, a manufacturing line, a production run, a production date, a bale, a warehouse, a customer, and/or a ship-to location. For example, the at least one supply chain component may represent a manufacturer of a portion of the standard fibers, and additionally or alternatively, a manufacturer of a portion of the identification fibers.

The method may also establish numbers of taggant chemical marker amounts for the one or more chemical markers included within the identification fibers. In some instances, the one or more chemical markers, the at least one taggant chemical marker amount, and/or the established numbers of taggant chemical marker amounts may be representative of the at least one component of a supply chain.

In one aspect, the method may receive, from a third party, information identifying (i) the one or more chemical markers, (ii) the at least one taggant chemical marker amount, and/or (iii) the established numbers of taggant chemical marker amounts.

In further aspects, the method may identify one or more proposed chemical markers, at least one proposed taggant chemical marker amount, and/or proposed numbers of taggant chemical marker amounts to represent the at least one component of the supply chain. The method may provide the one or more proposed chemical markers, the at least one proposed taggant chemical marker amount, and/or the proposed numbers of taggant chemical marker amounts to a third party, and may receive, from the third party, information indicative of an assignment of the one or more proposed chemical markers, the at least one proposed taggant chemical marker amount, and/or the proposed numbers of taggant chemical marker amounts to the at least one component of the supply chain. In other aspects, the method may assign the one or more proposed chemical markers, the at least one proposed taggant chemical marker amount, and/or the proposed numbers of taggant chemical marker amounts to the at least one component of the supply chain. The at least one component of the supply chain may, for example, correspond to a manufacturer.

The method may also generate correlation data mapping the one or more chemical markers, the at least one taggant chemical marker amount, and/or the numbers of taggant chemical marker amounts to the at least one supply chain component. In certain instances, the method may generate the correlation data by mapping the one or more chemical markers, the at least one taggant chemical marker amount, and/or numbers of taggant chemical marker amounts to the at least one supply chain component.

In one aspect, the method may generate the correlation data by generating a first structured list of the supply chain components, and generating a second structured list of one or more chemical markers available for inclusion within the identification fibers. The method may identify taggant chemical marker amounts that are available for inclusion within the identification fibers, and may generate a third structured list that includes combinations of the one or more available chemical markers and the available taggant chemical marker amounts. The method may also include mapping elements of the first structured list to elements of the second structured list, and mapping elements of the first structured list to elements of the third structured list. The method may store correlation data reflecting the mapping of the elements of the first and second structured lists and the mapping of the elements of the first and third structured lists.

In other aspects, the method may generate the correlation data by generating a first structured list of the supply chain components, and generating a second structured list of one or more chemical markers available for inclusion within the identification fibers. The method may also generate a third structured list of numbers of taggant chemical marker amounts capable of representing supply chain components. Further, the method may map elements of the first structured list to elements of the second structured list, and map elements of the first structured list to elements of the third structured list. The method may store correlation data reflecting the mapping of the elements of the first and second structured lists and the mapping of the elements of the first and third structured lists.

In one aspect, the method may obtain the standard fibers by producing at least a portion of the standard fibers on a first fiber production process. The first fiber production process may, for example, include a dry-spinning process, a solution-spinning process, a melt-spinning process, an electrospinning process, a gel-spinning process, a multi-component-spinning process, a melt-blowing process, and/or a solution-blowing process.

In additional aspects, the method may obtain the identification fibers by receiving at least a portion of the identification fibers from a third party and additionally or alternatively, by producing at least a portion of the identification fibers on a second fiber production process. The second fiber production process may, for example, include a dry-spinning process, a solution-spinning process, a melt-spinning process, an electro-spinning process, a gel-spinning process, a multi-component-spinning process, a melt-blowing process, and/or a solution-blowing process. In certain instances, the first production process and the second fiber production process correspond to a common fiber production process.

In some aspects, the method may produce the portion of the identification fibers by receiving an indication of one or more supply chain components to reflect in the identification fibers; accessing stored correlation data; identifying, from the stored correlation data, one or more chemical markers and/or at least one taggant chemical marker amount mapped to the one or more selected supply chain information components; selecting at least one manufacturing method associated with producing the identification fibers based on the one or more chemical markers and/or the at least one taggant chemical marker amount; and producing the identification fibers according to the selected at least one manufacturing method.

In one aspect, the method may select the at least one manufacturing method by determining whether an introduction of the one or more chemical markers and/or at least one taggant chemical marker amount into the identification fibers includes manipulating chemical properties of the identification fibers; identifying one or more manufacturing methods for the identification fibers based on the determination regarding introduction of the one or more chemical markers and/or the at least one taggant chemical marker amount into the identification fibers; and producing the identification fibers according to the identified one or more manufacturing methods.

The method may, for example, determine that the introduction of the one or more chemical markers and/or the at least one taggant chemical marker amount into the identification fibers includes at least a manipulation of chemical properties. In response to the determination, the method may identify the one or more chemical markers for inclusion within the identification fibers, and select at least one manufacturing method capable of producing the identification fibers with the identified one or more chemical markers.

The one or more chemical markers may, for example, be selected from a group consisting of one or more taggant non-volatile organic compounds, one or more taggant photoluminescent materials, one or more taggant polymeric additives, one or more taggant carbohydrates, one or more taggant metal oxides, one or more taggant inorganic salts, one or more taggant optical isomers, one or more taggant isotopically labeled molecules, or one or more taggant trace chemicals inherent to a manufacturer of the fiber band.

In some aspects, the at least one manufacturing method may include one or more of applying the chemical markers to the identification fibers by a method selected from a group consisting of dipping, immersing, submerging, soaking, rinsing, washing, painting, coating, showering, drizzling, spraying as a liquid, spraying as an atomized substance, placing, dusting, sprinkling, affixing, pouring, or direct metering.

In further aspects, the at least one manufacturing method may include applying the one or more of chemical markers in a form selected from the group consisting of neat, in a solution, in an emulsion, and in a suspension. The at least one manufacturing may also include adding the one or more chemical markers to a spinning solution upstream of at least one of a production line, spinning cabinets, or individual spinnerets.

In additional embodiments, a method for identifying supply chain information from fiber samples includes analyzing a fiber sample for identification fibers. The method may identify one or more chemical markers associated with the sample from the identification fibers, and may determine a chemical marker amount associated with each of the chemical markers. In one aspect, the determined chemical marker amounts include at least one taggant chemical marker amount. The method may access correlation data mapping components of a supply chain to the one or more identified chemical markers and/or the at least one taggant chemical marker amount. Based on the accessed correlation data and the one or more identified chemical markers and/or the at least one taggant chemical marker amount, the method may identify at least one component of the supply chain associated with the fiber sample.

In certain aspects, the fiber sample may include standard fibers and the identification fibers, and the supply chain components may include a manufacturer, a manufacture site, a manufacturing line, a production run, a production date, a bale, a warehouse, a customer, and/or a ship-to location. Further, by way of example, the at least one identified supply chain component may include a manufacturer, a manufacture site, a manufacturing line, a production run, a production date, a bale, a warehouse, a customer, and/or a ship-to location.

Further, for example, the fiber sample may include cellulose acetate fibers, and additionally or alternatively, may include a portion of a cellulose acetate tow band. In other instances, the fiber sample may include a portion of at least one of a filter rod or cigarette filter. The fiber sample may also include a portion of at least one of a textile product, a woven fabric, a non-woven fabric, or an absorbent product.

In some aspects, the method may receive a request to identify supply chain information associated with the fiber sample from a requesting entity, and may transmit information identifying the at least one supply chain component to the requesting entity. The requesting entity may, for example, include a manufacturer, a customer, a governmental entity, a law enforcement entity, and/or a third-party requestor.

In additional aspects, the method may identify a plurality of supply chain components based on the accessed correlation data and the one or more identified chemical markers and/or the at least one taggant chemical marker amount, and may transmit information identifying a subset of the plurality of supply chain components to the requesting entity. Further, the method may also transmit, to the requesting entity, information identifying a manufacturer and additionally or alternatively, information identifying at least a portion of the one or more identified chemical markers and/or the at least one taggant chemical marker amount.

In other aspects, the method may identify the one or more chemical markers by selecting a solvent for conducting a chemical analysis; dissolving the sample in the selected solvent to produce a sample solution; analyzing the sample solution; identifying the one or more chemical markers in the sample solution based on the analysis; and identifying at least one measurable gradation for each of the one or more identified chemical markers based on the analysis.

The method may determine that one or more fibers from the sample did not dissolve in the solvent. In response to the determination, the method may analyze the one or more undissolved fibers and identify at least one observable chemical marker based on the analysis.

In additional aspects, the method may analyze the one or more undissolved fibers by selecting at least one additional solvent for conducting the chemical analysis, and dissolving at least one of the undissolved fibers in the at least one additional solvent to produce the sample solution. By way of example, the solvent and at least one additional solvent are selected from a group consisting of one or more of ethers; ketones; aliphatic and aromatic hydrocarbons with or without heteroatoms comprising halogens, amines, oxygen, sulfur or phosphorus; water; or ionic liquids. In other instances, the solvent and at least one additional solvent are selected from a group consisting of one or more of acetone, tetrahydrofuran, dichloromethane, methanol, chloroform, dioxane, N,N-dimethylformamide, dimethyl sulfoxide, methyl acetate, ethyl acetate, or pyridine.

The method may, in some aspects, analyze the sample solution using use of one or more of mass spectrometry, spectroscopy, nuclear magnetic resonance, x-ray diffraction, or chromatography. Further, the method may analyze the sample solution by selecting at least one analysis technique, characterizing each chemical marker from the one or more identified chemical markers according to the selected at least one analysis technique; identifying a concentration for each of the one or more identified chemical markers; generating a deconvoluted spectra based on the one or more characterized chemical markers and the one or more identified concentrations; determining whether multiple chemical markers are present among the one or more identified chemical markers; and determining whether non-volatile compounds are present in the sample solution.

When the multiple chemical markers are determined to be present, the method may further analyze sample solution by extracting a serial number from the deconvoluted spectra. Additionally, when non-volatile compounds are determined to be present, the method may further analyze the sample solution by identifying molecular constituents of at least one non-volatile compound present in the sample solution, and determining a quantity of each non-volatile compound from the at least one non-volatile compound.

In certain exemplary embodiments described above, methods for embedding supply chain information obtain standard fibers and identification fibers, and further, combine the obtained standard fibers with the obtained identification fibers for form fibers and/or fiber products. The disclosed embodiments are, however, not limited to methods combine standard and identification fibers for form fibers and/or fiber products. In other embodiments, the exemplary methods outlined above may embed supply chain information into fibers and/or fiber products that include only identification fibers. For example, exemplary methods for embedding supply chain information into fibers may include obtaining identification fibers that include one or more chemical markers. Each of the chemical markers may be present within the identification fibers in a corresponding chemical marker amount, and at least one of the chemical marker amounts may represent a taggant chemical marker amount. In certain aspects, the obtained identification fibers may represent the fibers, which may be incorporated into a fiber product, and the one or more chemical markers and/or the at least one taggant chemical marker amount may be representative of at least one component of a supply chain.

Figure 1B:
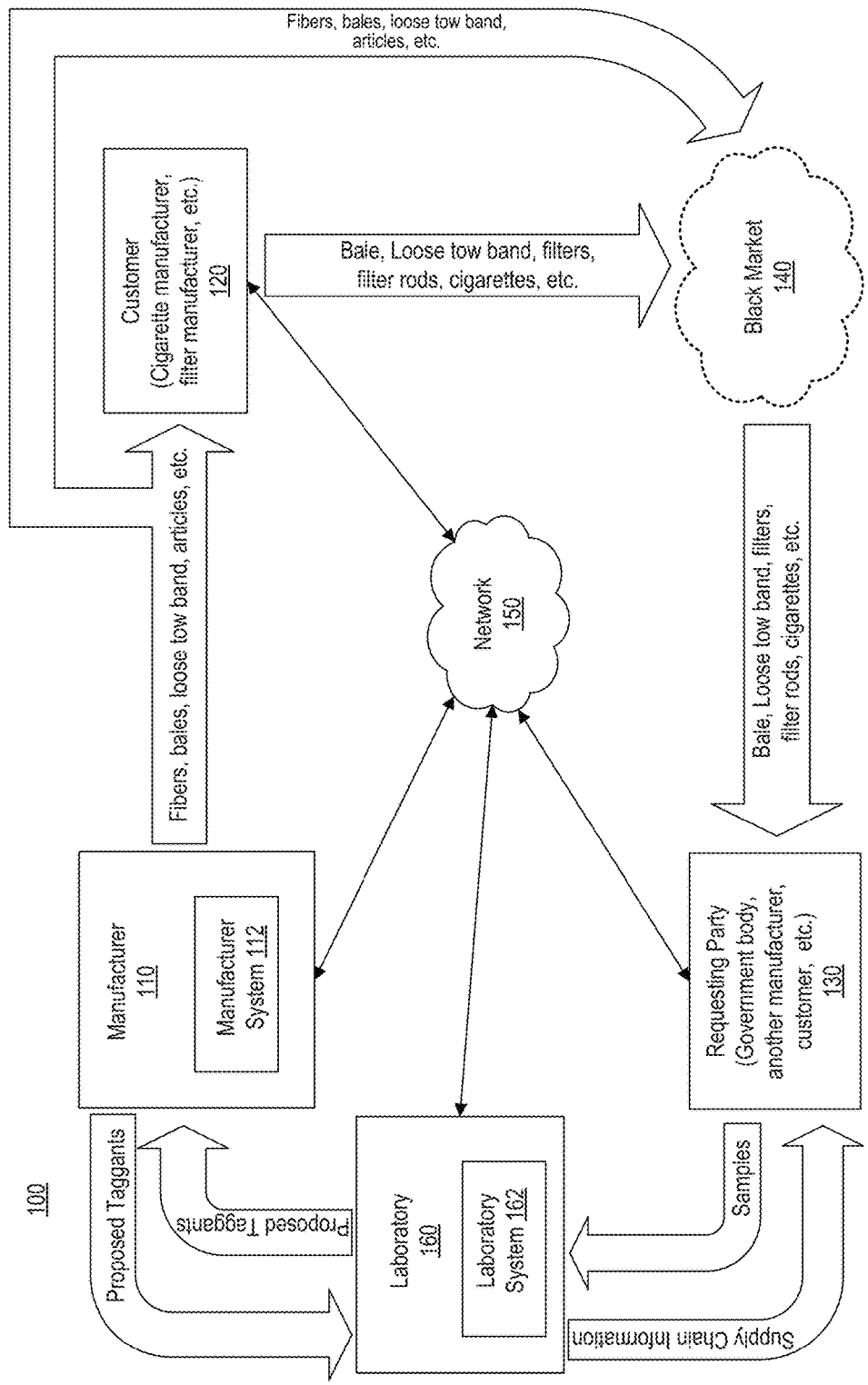

FIGS. 1A and 1B illustrate non-limiting examples of an environment 100 depicting communication and shipping channels among entities consistent with disclosed embodiments. In one embodiment, environment 100 of FIGS. 1A and 1B may include one or more manufacturers 110, one or more customers 120, a black market 140 or other illicit trade network, one or more requesting parties 130, one or more laboratories 160, and communication network 150. The components and arrangement of the components included in environment 100 (e.g., as illustrated in FIGS. 1A and 1B) may vary. Thus, environment 100 may include other components that perform or assist in the performance of one or more processes consistent with the disclosed embodiments.

In some aspects, network 150 may be any type of network configured to provide communication means between systems of components of environment 100 (e.g., manufacturing system 112 and/or laboratory system 162). For example, network 150 may be any type of network (including infrastructure) that facilitates communications, exchanges information, etc., such as the Internet, a Local Area Network, near field communication, and/or other suitable connection(s) that enables the sending and receiving of information between the component systems associated with environment 100. In other embodiments, one or more component systems of environment 100 may communicate directly through a dedicated communication link(s), such as links between manufacturer 110, customer 120, requesting party 130, and/or laboratory 160.

Further, and as stated above, manufacturers (e.g., manufacturer 110) may produce cellulose acetate fibers and fiber products that incorporate the cellulose acetate fibers on an industrial scale. In some embodiments, the produced cellulose acetate fibers and fiber products may include standard fibers and identification fibers. The identification fibers may include one or more chemical markers present in corresponding chemical marker amounts. Further, at least one of the chemical marker amounts may represent a taggant chemical marker amount, which may distinguish the identification fibers from the standard fibers. As stated above, the at least one taggant chemical marker amount may be selected from a number of taggant chemical marker amounts appropriate for inclusion within the identification fibers. In certain aspects, the chemical markers, the at least one taggant chemical marker amount, and/or the number of taggant chemical marker amounts may be representative of at least one supply chain component associated with fibers or fiber products, including cellulose acetate fibers and fiber products.

In some embodiments, the inclusion of identification fibers in the cellulose acetate fibers may enable manufacturer 110 to tag the cellulose acetate fibers, and thus, the fiber products that include the cellulose acetate fibers, with supply chain information prior to shipment to customers 120. By way of example, fiber products consistent with the disclosed embodiments may include, but are not limited to, cellulose acetate tow, loose bands of cellulose acetate tow, bales of cellulose acetate tow, and fabrics and other articles that include the cellulose acetate fibers and/or tow.

For example, and in the context of cigarette manufacturing, customer 120 may use a bale of acetate tow to produce various intermediate and/or final stage products (e.g., loose tow band, filter rods, filters, and/or cigarettes) and a fraction of these products can ultimately find their way onto the black market (e.g., black market 140). Thus, because supply chain information can be determined from a sample of any black market product having tagged identification fibers, a party interested in combating illicit trade (e.g., requesting party 130) may obtain a black market product and submit a sample for analysis in order to identify supply chain information associated with the black market product.

Thus, in one embodiment, requesting party 130 may provide the sample to manufacturer 110, as depicted in FIG. 1A. Manufacturer 110 may, in certain aspects, analyze the sample to identify at least one component of a supply chain associated with the sample. For example, the sample may include standard and identification fibers, and in some instances, manufacturer 110 may analyze the sample using any of the exemplary techniques outlined above.

Based on the analysis, manufacturer 110 may identify one or more chemical markers present within the identification fibers, and further, may identify at least one taggant chemical marker amount associated with one or more of the identified chemical markers. In certain aspects, manufacturer 110 may access correlation data mapping components of the supply chain to the identified chemical markers and/or the at least one identified taggant chemical marker amount. Manufacturer 110 may identify the at least one component of the supply chain based on, for example, a comparison of the identified chemical markers and/or the at least one identified taggant chemical marker amount to the accessed correlation data. In some instances, manufacturer 110 may transmit information identifying the at least one supply chain component to requesting party 130 (e.g., across network 150).

In the exemplary embodiments described above, manufacturer 110 may analyze the sample to identify at least one component of a supply chain associated with the sample. The disclosed embodiments are, however, not limited to exemplary analyses conducted by manufacturer 110, and in further embodiments, customer 120, requesting party 130, or a third-party (not shown) may conduct the analysis for identifying supply chain information from tagged fibers.

For example, as illustrated in FIG. 1B, a laboratory 160 may act on behalf of requesting party 130 and perform the analysis on the sample to identify the at least one supply chain component associated with the sample. In some instances, laboratory 160 may represent a governmental entity, a quasi-governmental entity, or a private entity capable of performing the analysis, and requesting party 130 may contract with or retain laboratory 160 to perform the analysis on a one-time or recurring basis.

In other instances, however, laboratory 160 may be established by one of more of manufacturer 110, customers 120, and/or requesting party 130 in order to regularly and reliably identify supply chain components associated with samples taken from illicitly traded cellulose acetate fibers or fiber products that incorporate the cellulose acetate fibers (e.g., as obtained by requesting party 130 from black market 140). Laboratory 160 may, in certain aspects, perform the analysis of the sample in accordance with one or more procedures established by a manufacturer 110, customers 120, and/or requesting party 130. For example, one or more of manufacturer 110, customers 120, and/or requesting party 130 may collectively establish standardized procedures and protocols for receiving and handling samples, analyzing the samples to identify the supply chain components in an accurate and repeatable manner, and reporting portions of the identified supply chain components to manufacturer 110, customers 120, and/or requesting party 130. Further, in additional embodiments, laboratory 160 may also assign the chemical markers, the at least one taggant chemical marker amount, and additionally or alternatively, the numbers of taggant chemical marker amounts to various components of the supply chain (e.g., manufacturers) to uniquely identify these supply chain components. In further embodiments, customer 120, requesting party 130, or a third-party (not shown) may assign a portion of the chemical markers, the at least one taggant chemical marker amount, and/or the numbers of taggant chemical marker to various components of the supply chain (e.g., manufacturers) to uniquely identify these supply chain components.

In one embodiment, as illustrated in FIG. 1B, requesting party 130 may provide the sample to laboratory 160. Laboratory 160 may, in certain aspects, analyze the sample to identify at least one component of a supply chain associated with the sample (e.g., a manufacturer). For example, using any of the exemplary techniques described above, laboratory 160 may analyze the sample to identify chemical markers and further, at least one taggant chemical marker amount present within the sample. Further, laboratory 160 may access correlation data, and using any of the exemplary techniques described above, identify the at least one supply chain component based on a comparison of the chemical markers and/or the at least one taggant chemical marker amount to the accessed correlation data.

In additional embodiments, laboratory 160 may function as a centralized facility that assigns unique chemical markers, taggant chemical marker amounts, and/or numbers of taggant chemical marker amounts to various components of the supply chain (e.g., to manufacturer 110). For example, laboratory 160 may assign one or more chemical markers and at least one taggant chemical marker amount to manufacturer 110.

When present in identification fibers included within cellulose acetate fibers and corresponding fiber products produced by manufacturer 110, the assigned chemical markers and/or at least one taggant chemical marker amount may uniquely represent manufacturer 110 and may enable laboratory 160 (and additionally or alternatively, any other entity within environment 100) to identify manufacturer 110 as a source of the fiber products using any of the analytical techniques described above. Further, laboratory 160 (and additionally or alternatively, any other entity within environment 100) may also establish and maintain data records (e.g., within a centralized database implemented using the exemplary computing systems outlined below) that identify a correlation between the various supply chain components (e.g., manufacturer 110) and the assigned chemical markers and at least one taggant chemical marker amount (and additionally or alternative, one or more assigned numbers of taggant chemical marker amounts).

In certain aspects, laboratory 160 may establish a centralized repository for data and data records (e.g., using any of the exemplary computing systems outlined below) that correlate the various supply chain components (e.g., manufacturer 110) to corresponding ones of chemical markers, taggant chemical marker amounts, and/or numbers of taggant chemical marker amounts. Further, in other aspects, laboratory 160 may access the centralized repository and generate one or more reports specifying the chemical markers, taggant chemical marker amounts, and/or numbers of taggant chemical marker amounts that uniquely identify at least one of the supply chain components (e.g., manufacturers). Laboratory 160 may, in some instances, generate the reports at predetermined intervals or in response to received requests (e.g., from requesting party 130, manufacturer 110, etc.), and may provide the generated reports to various parties and entities within environment 100 (e.g., across network 150).

In some embodiments, laboratory 160 may access the centralized repository to identify at least one supply chain component (e.g., manufacturer 110) associated with at least one chemical marker and/or at least one taggant chemical marker amount identified by laboratory 160 (e.g., using any of the analytical techniques outlined above) and additionally or alternatively, obtained from any third party or other entity within environment 100. Further, and as described below, the centralized repository may enable laboratory 160 to determine whether proposed chemical markers, taggant chemical marker amounts, and/or numbers of taggant chemical marker amounts (e.g., as selected by manufacturer 110) are capable of uniquely representing fibers and fiber products of manufacturer 110 that are introduced into the supply chain.

In certain embodiments, laboratory 160 may receive proposed chemical markers, taggant chemical marker amounts, and/or numbers of taggant chemical marker amounts from manufacturer 110. Laboratory 160 may, for example, compare the proposed chemical markers, taggant chemical marker amounts, and/or numbers of taggant chemical marker amounts against the established data records (e.g., within the centralized repository) to determine whether these proposed chemical markers, taggant chemical marker amounts, and/or numbers of taggant chemical marker amounts are capable of uniquely identifying manufacturer 110 (e.g., that the proposed chemical markers, taggant chemical marker amounts, and/or numbers of taggant chemical marker amounts are assigned to no other supply chain components, such as another manufacturer). If the proposed chemical markers, taggant chemical marker amounts, and/or numbers of taggant chemical marker amounts could uniquely represent manufacturer 110, laboratory 160 may assign the proposed chemical markers, taggant chemical marker amounts, and/or numbers of taggant chemical marker amounts to manufacturer 110, update the data records to reflect the assignment, and provide confirmation of the assignment to manufacturer 110 (e.g., between computing systems of laboratory 160 and manufacturer 110 across network 150).

Alternatively, if laboratory 160 previously assigned the proposed chemical markers, taggant chemical marker amounts, and/or numbers of taggant chemical marker amounts to another manufacturer (or the proposed chemical markers, taggant chemical marker amounts, and/or numbers of taggant chemical marker amounts are inappropriate to represent manufacturer 110), laboratory 160 may assign alternate chemical markers, taggant chemical marker amounts, and/or numbers of taggant chemical marker amounts to manufacturer 110, update the data records to reflect the alternate assignment, and provide confirmation of the alternate assignment to manufacturer 110. In other aspects, laboratory 160 could provide, to manufacturer 110, an indication of the assignment of the proposed chemical markers, taggant chemical marker amounts, and/or numbers of taggant chemical marker amounts to another manufacturer, and request that manufacturer 110 propose additional chemical markers, taggant chemical marker amounts, and/or numbers of taggant chemical marker amounts for assignment by laboratory 160, as described above.

In certain aspects, upon confirmation of the assignment, manufacturer 110 may obtain and/or produce identification fibers that include the assigned chemical markers. For example, the assigned chemical markers may be present within the obtained or produced identification fibers in corresponding chemical marker amounts (e.g., by weight of the identification fibers), at least a portion of which correspond to the assigned taggant chemical marker amounts.

In other aspects, however, manufacturer 110 may further correlate the assigned chemical markers, taggant chemical marker amounts, and/or numbers of taggant chemical marker amounts to one or more upstream components of the supply chain (e.g., a manufacture site, a manufacturing line, a production run, a production date, a bale) and/or various downstream components of the supply chain (e.g., a warehouse, a customer, a ship-to location, etc.). For example, manufacturer 110 may further specify assigned one or more of chemical markers, taggant chemical marker amounts, and/or numbers of taggant chemical marker amounts to uniquely represent a particular customer within the supply chain (e.g., customer 120).

The disclosed embodiments are, however, not limited to techniques that enable manufacturer 110 to correlate customer 120 to assigned chemical markers, taggant chemical marker amounts, and/or numbers of taggant chemical marker amounts. In further embodiments, manufacturer 110 may specify any additional or alternate taggant information to represent other upstream or downstream supply components (or combinations thereof) in conjunction with the assigned chemical markers, taggant chemical marker amounts, and/or numbers of taggant chemical marker amounts.

In some aspects, while laboratory 160, or another entity, may maintain information linking manufacturer 110 to assigned chemical markers, taggant chemical marker amounts, and/or numbers of taggant chemical marker amounts, manufacturer 110 may hold confidential additional taggant information (e.g., non-assigned chemical markers, non-assigned taggant chemical marker amounts, etc.) that links identification fibers, and thus fiber products produced by manufacturer 110, to other upstream and downstream components of the supply chain. The confidentiality of the additional taggant information may, in certain instances, enable manufacturer 110 to prevent laboratory 160 from identifying customers (e.g., customer 120), ship-to locations, warehouses, and other internal supply chain components (e.g., manufacture site or line, and production run or date) associated with manufacturer 110.

The embodiments described above identify particular combinations of taggant information that correlate to a specific component of a supply chain and, when present in identification fibers of a sample, enable a laboratory, a manufacturer, or other entities to identify the specific supply chain component associated with the sample. One of ordinary skill in the art would, however, understand that the disclosed embodiments are not limited to the particular combinations or taggant information outlined above, and in further embodiments, specific supply chain components may be correlated with any additional or alternate physical, chemical, and/or optical characteristic exhibited by the identification fibers. Moreover, while not depicted in FIGS. 1A and 1B, one of skill in the art would understand that entities associated with environment 100 (shown and not shown) may employ one or more warehouses to store raw materials, intermediate products, final stage products, etc. in conducting operations consistent with disclosed embodiments.

Figure 2:
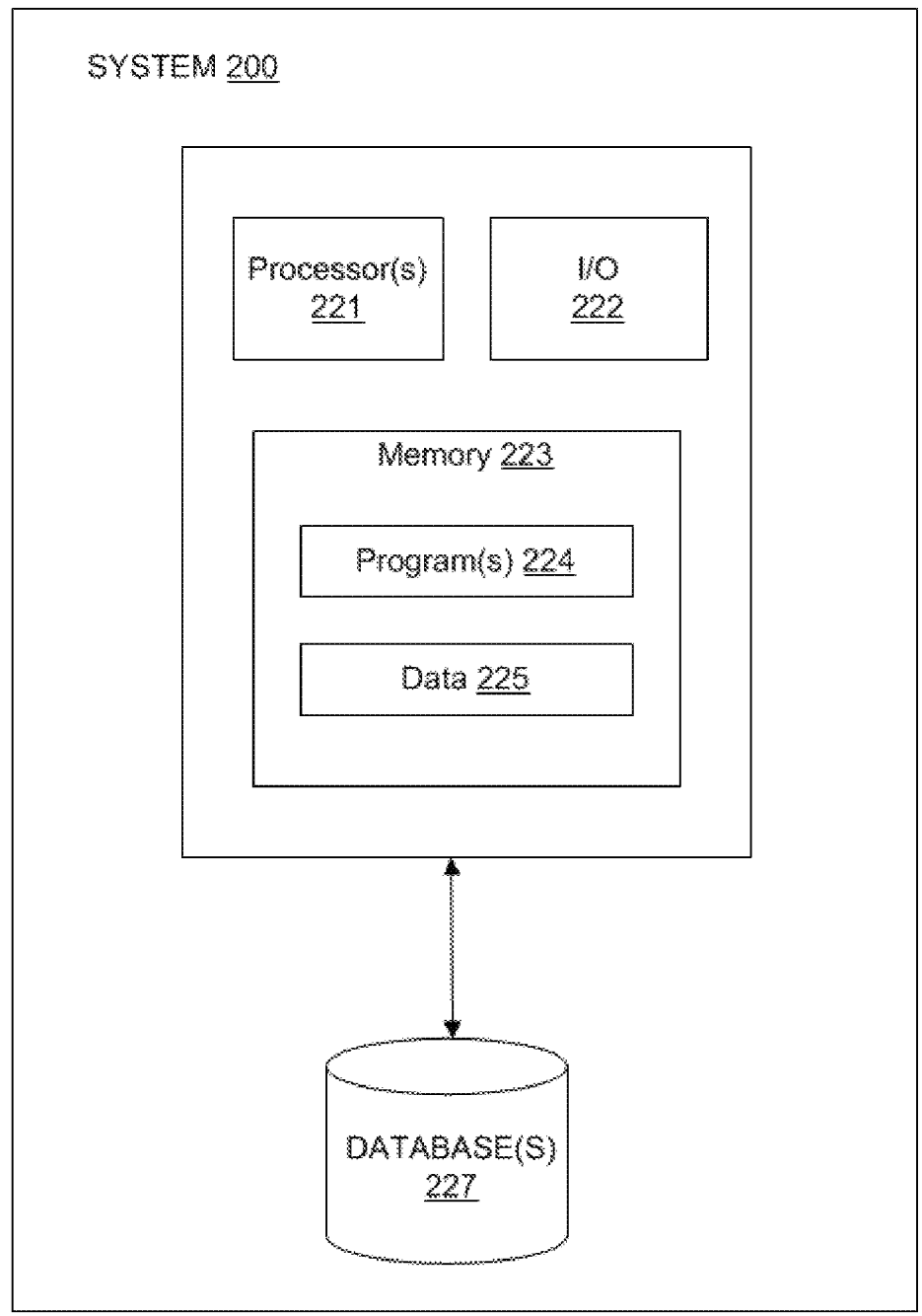
FIG. 2 illustrates a non-limiting example of a computing system used by one or more entities consistent with disclosed embodiments.

FIG. 2 illustrates a non-limiting example of a computing system 200 used by one or more entities consistent with disclosed embodiments. Variations of exemplary system 200 may be used by manufacturer 110 (e.g., as manufacturer system 112), customer 120, requesting party 130, and/or laboratory 160 (e.g., as laboratory system 162). In one embodiment, system 200 may comprise one or more processors 221, one or more input/output (I/O) devices 222, and one or more memories 223. In some embodiments, system 200 may take the form of a server, mainframe computer, or any combination of these components. In some embodiments, system 200 may take the form of a mobile computing device such as a smartphone, tablet, laptop computer, or any combination of these components. Alternatively, system 200 may be configured as a particular apparatus, embedded system, dedicated circuit, and the like based on the storage, execution, and/or implementation of the software instructions that perform one or more operations consistent with the disclosed embodiments.

Processor 221 may include one or more known processing devices, such as mobile device microprocessors or any various other processors. The disclosed embodiments are not limited to any type of processor(s) configured in system 200.

Memory 223 may include one or more storage devices configured to store instructions used by processor 224 to perform functions related to the disclosed embodiments. For example, memory 223 may be configured with one or more software instructions, such as program(s) 224 that may perform one or more operations consistent with disclosed embodiments when executed by processor 221. The disclosed embodiments are not limited to separate programs or computers configured to perform dedicated tasks. For example, memory 223 may include a single program 224 that performs the functions of system 200, or program 224 may comprise multiple programs. Memory 223 may also store data 225 that is used by one or more programs 212, such as correlation data mapping distinct features to one or more components of the supply chain information.

I/O devices 222 may be one or more devices configured to allow data to be received and/or transmitted by system 200. I/O devices 222 may include one or more digital and/or analog devices that allow components of environment 100 to communicate with other machines and devices, such as other components of environment 100. For example, I/O devices 222 may include a screen for displaying messages, distinct feature information, supply chain information, or providing other information to the user, such as an employee of manufacturer 110, customer 120, requesting party 130, and/or laboratory 160. I/O devices 222 may also include one or more digital and/or analog devices that allow a user to interact with system 200 such as a touch-sensitive area, keyboard, buttons, or microphones. I/O devices 222 may also include other components known in the art for interacting with a user.

The components of system 200 may be implemented in hardware, software, or a combination of both hardware and software, as will be apparent to those skilled in the art. For example, although one or more components of system 200 may be implemented as computer processing instructions, all or a portion of the functionality of system 200 may be implemented instead in dedicated electronics hardware.

System 200 may also be communicatively connected to one or more database(s) 227. System 200 may be communicatively connected to database(s) 227 through network 150. Database 227 may include one or more memory devices that store information and are accessed and/or managed through system 200. By way of example, database(s) 227 may include Oracle™ databases, Sybase™ databases, or other relational databases or non-relational databases, such as Hadoop sequence files, HBase, or Cassandra.

Systems and methods of disclosed embodiments, however, are not limited to separate databases. In one aspect, system 200 may include database 227. Alternatively, database 227 may be located remotely from the system 200. Database 227 may include computing components (e.g., database management system, database server, etc.) configured to receive and process requests for data stored in memory devices of database(s) 227 and to provide data from database 227.

Although the above description has designated laboratory 160 as the entity assigning various taggant information, in other aspects, manufacturer 110, customer 120, requesting party 130 or a third-party entity not shown may be the one assigning taggants for identification fibers. Furthermore, as seen from FIGS. 1A and 1B, although the description has focused on cellulose acetate tow and the black market associated with cigarette filters, the embodiments clearly apply to fibers of any material and any article subject to illicit trade.

Figure 3:
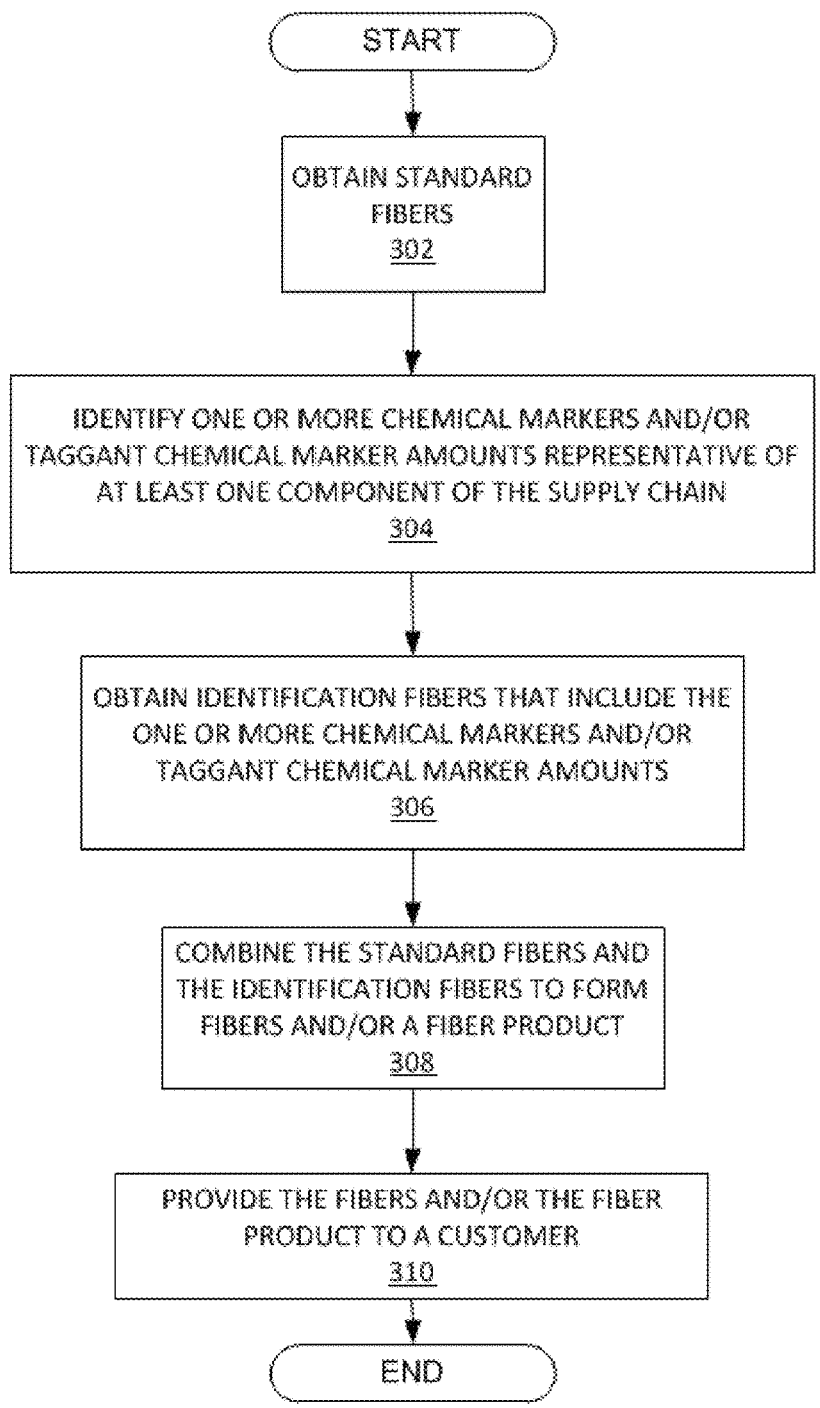
FIG. 3 illustrates a non-limiting example of a process for embedding supply chain information into fibers.

FIG. 3 illustrates a non-limiting example of a process for embedding supply chain information into fibers, as seen and described above with respect to disclosed embodiments.

Figure 4:
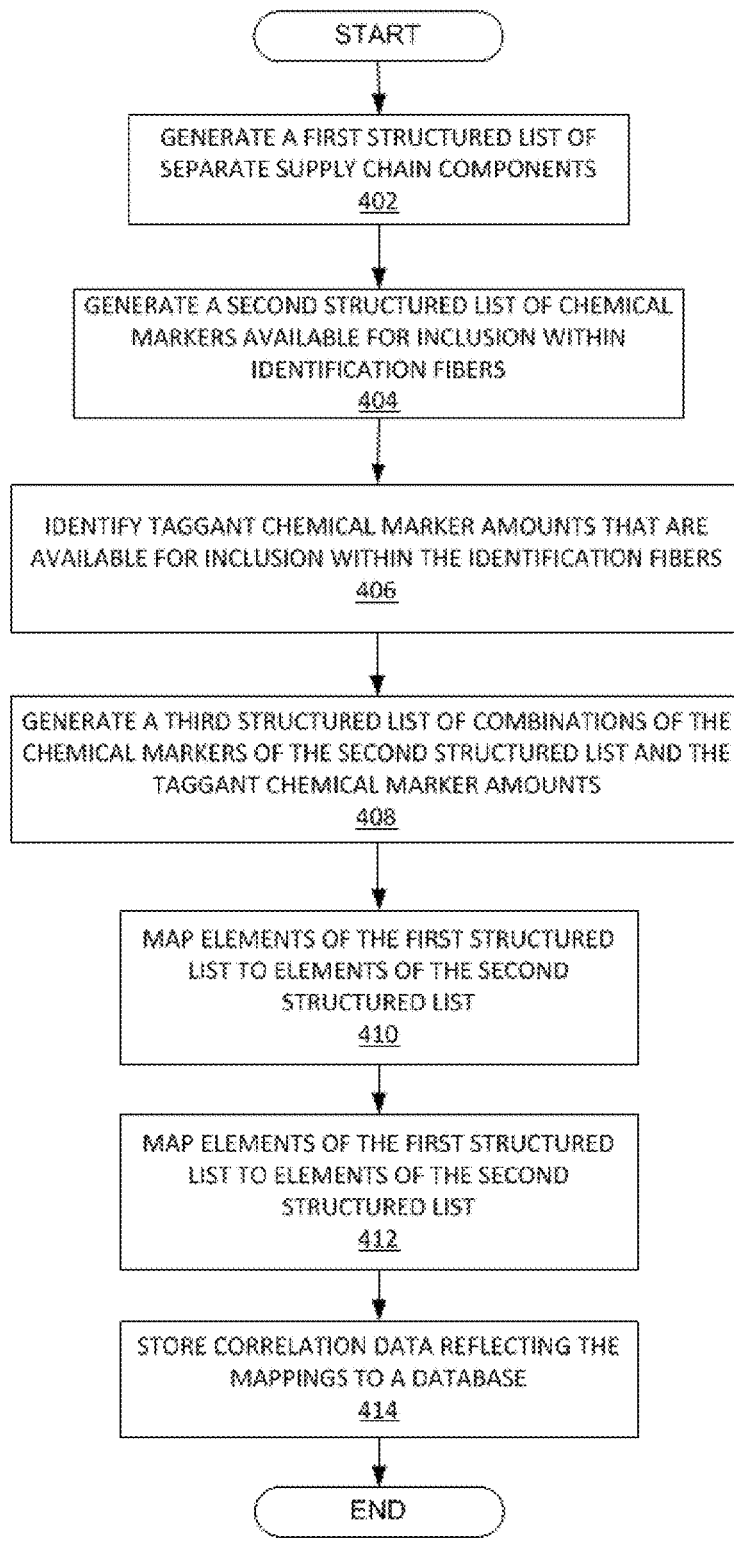
FIG. 4 illustrates a non-limiting example of a process for generating correlation data mapping chemical markers to supply chain information.

FIG. 4 illustrates a non-limiting example of a process for generating correlation data, as seen and described above with respect to disclosed embodiments. For example, as described in FIG. 4, manufacturer 110 (and additionally or alternatively, laboratory 160) may generate a first structured list of the supply chain components having one or more corresponding attributes, and may generate a second structured list of chemical markers available for inclusion within identification fibers. In some aspects, manufacturer 110 may identify one or more taggant chemical marker amounts that are available and appropriate for inclusion within the identification fibers (e.g., as selected from an assigned number of taggant chemical marker amounts for the available chemical markers), and may generate a third structured list of combinations of the chemical markers included in the first structured list and the one or more taggant chemical marker amounts. Manufacturer 110 may also map (i) elements of the first structured list to elements of the second structured list and (ii) elements of the first structured list to elements of the third structured list. Manufacturer 110 may, in additional aspects, store correlation data (e.g., in database 227) reflecting the mapping of the elements of the first and second structured lists and the mapping of the elements of the first and third structured lists.

Figure 5:
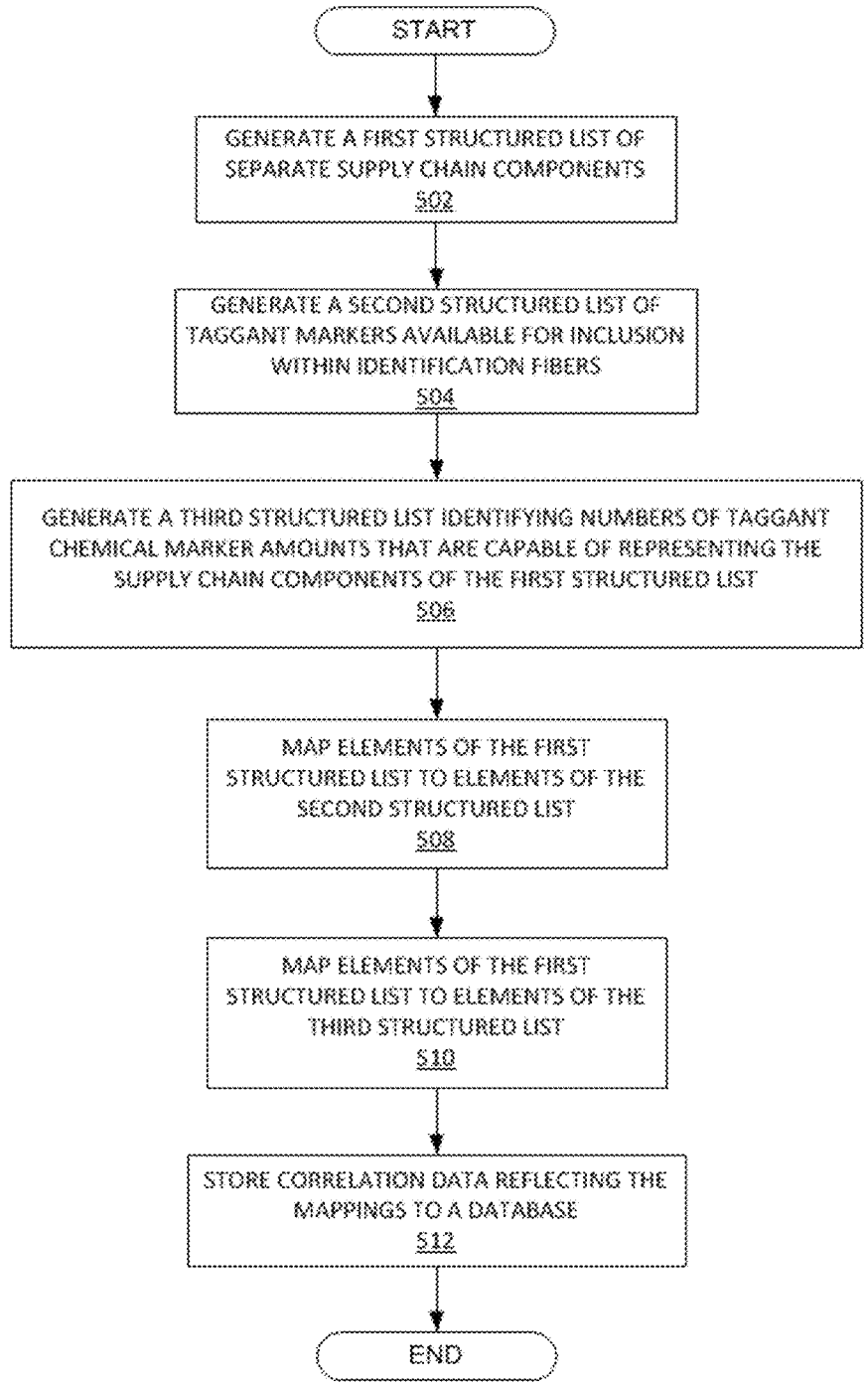
FIG. 5 illustrates a non-limiting example of a process for generating correlation data mapping chemical markers to supply chain information.

FIG. 5 illustrates a non-limiting example of a process for generating correlation data, as seen and described above with respect to disclosed embodiments. For example, as described in FIG. 5, manufacturer 110 (and additionally or alternatively, laboratory 160) may generate a first structured list of the supply chain components having one or more corresponding attributes, and may generate a second structured list of chemical markers available for inclusion within identification fibers. In some aspects, manufacturer 110 may generate a third structured list identifying numbers of taggant chemical marker amounts (e.g., of the available chemical markers) that are capable of representing the supply chain components included within the first structured list. Manufacturer 110 may also map (i) elements of the first structured list to elements of the second structured list and (ii) elements of the first structured list to elements of the third structured list. Manufacturer 110 may, in additional aspects, store correlation data (e.g., in database 227) reflecting the mapping of the elements of the first and second structured lists and the mapping of the elements of the first and third structured lists.

Figure 6:
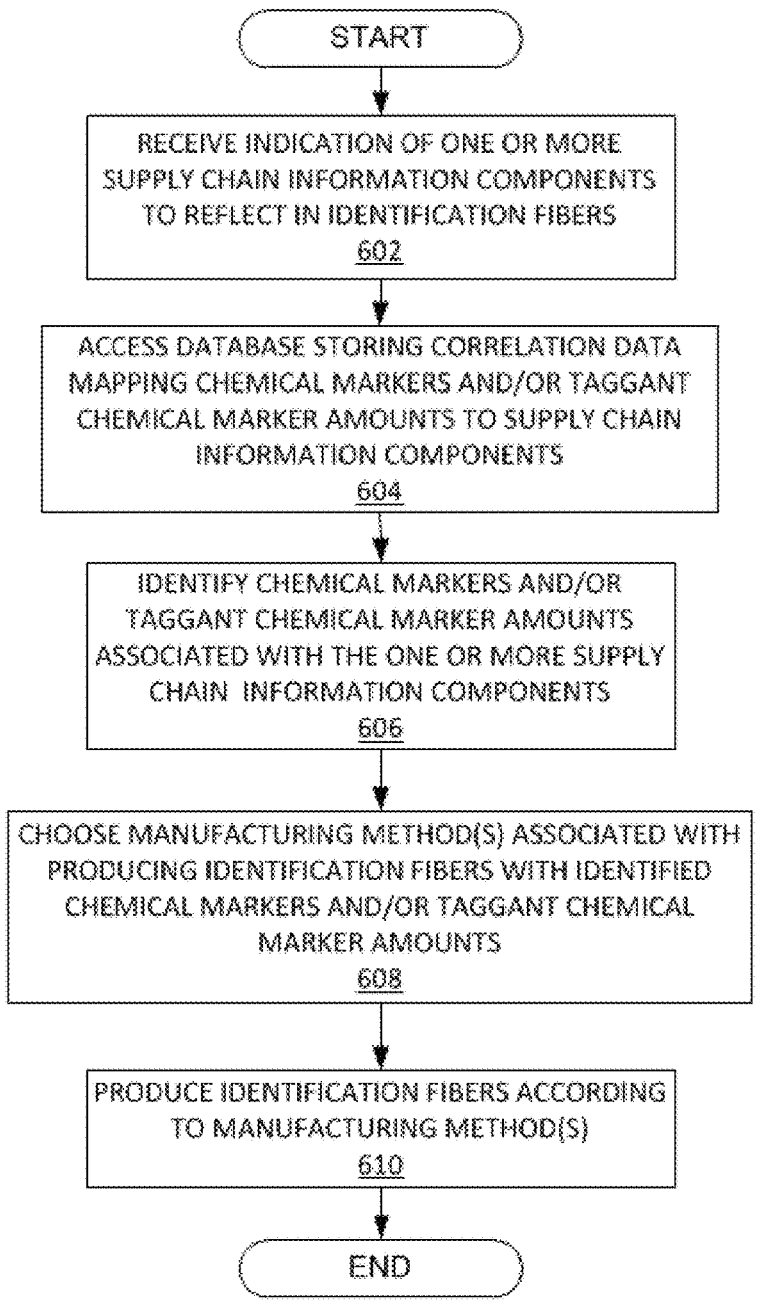
FIG. 6 illustrates a non-limiting example of a process for producing identification fibers.

FIG. 6 illustrates a non-limiting example of a process for producing identification fibers, as seen and described above with respect to disclosed embodiments.

Figure 7:
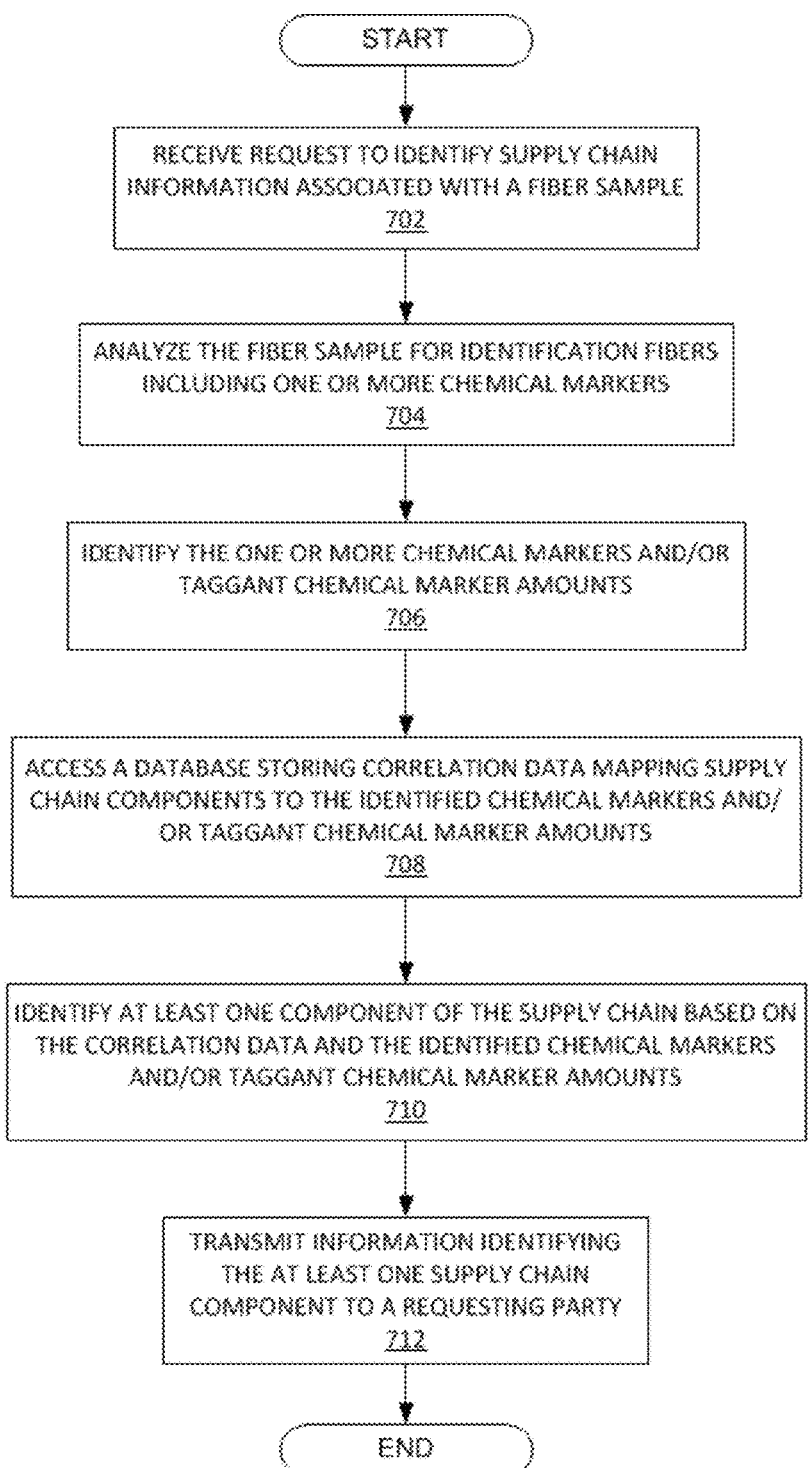
FIG. 7 illustrates a non-limiting example of a process for identifying supply chain information from a sample.

FIG. 7 illustrates a non-limiting example of a process for identifying at least one supply chain component associated with a fiber sample, as seen and described above with respect to disclosed embodiments.

Figure 8:
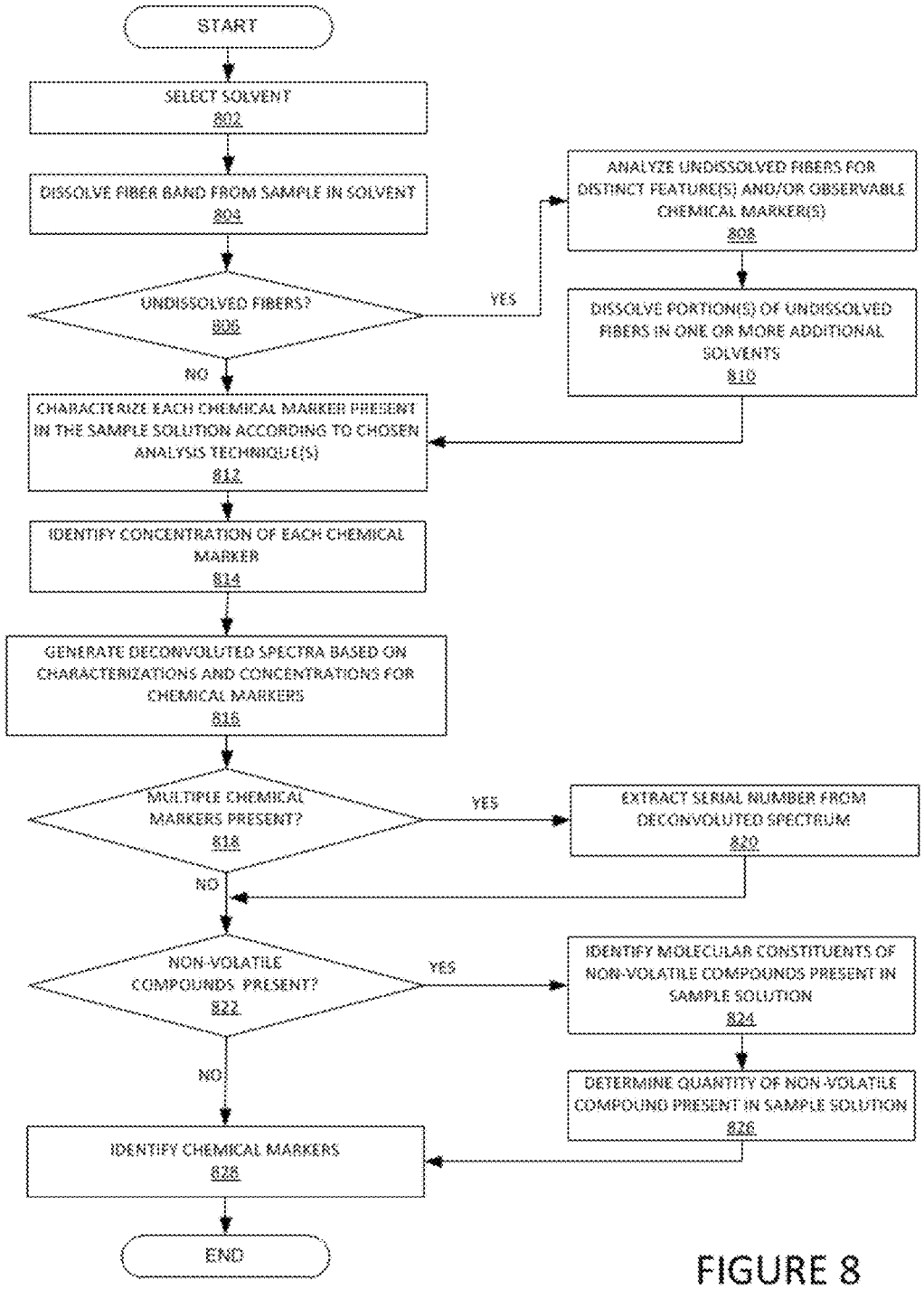
FIG. 8 illustrates a non-limiting example of a process for identifying chemical markers from identification fibers.

FIG. 8 illustrates a non-limiting example of a process for identifying chemical markers from identification fibers, as seen and described above with respect to disclosed embodiments.

Figure 9:
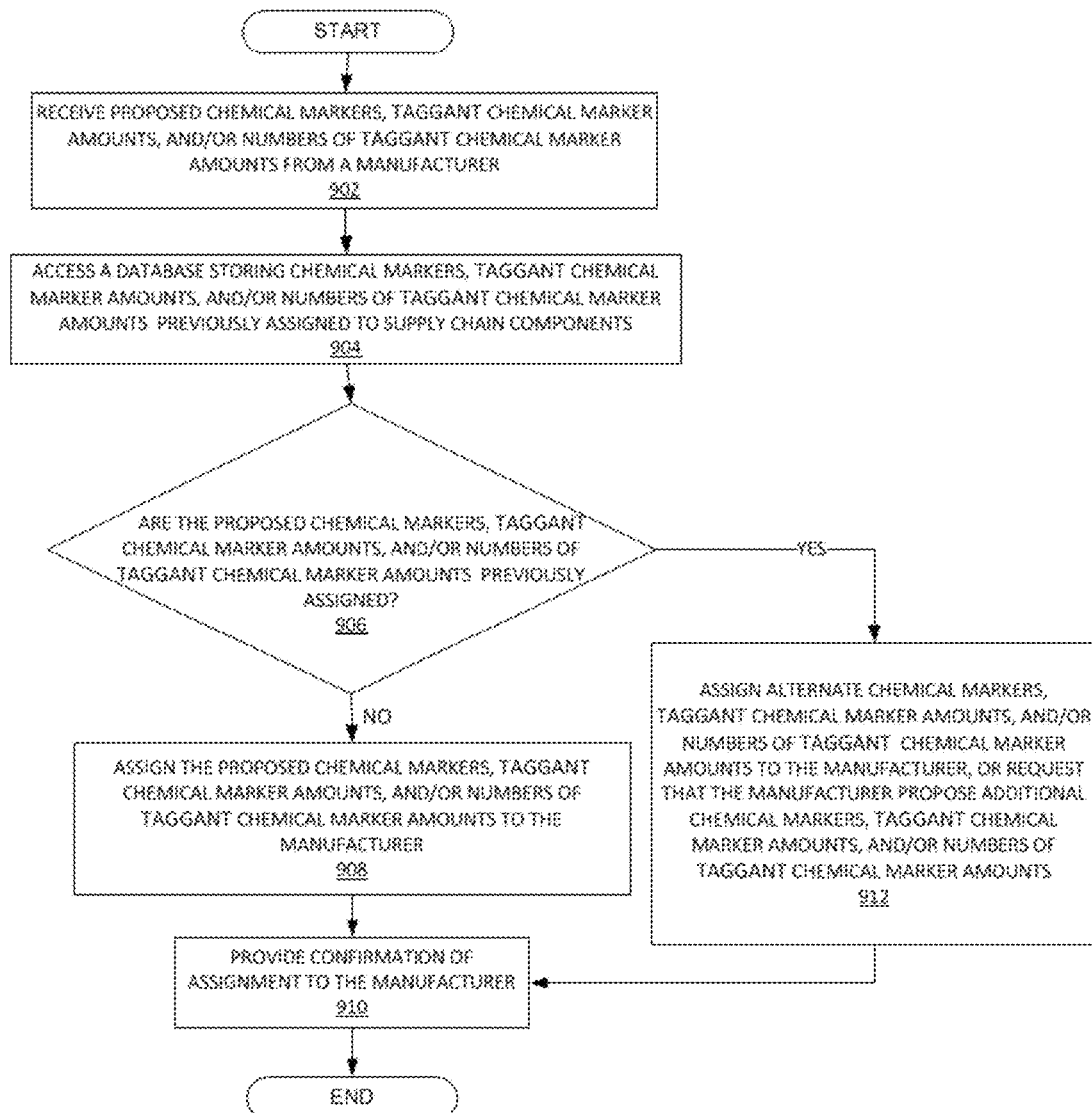
FIG. 9 illustrates a non-limiting example of a process for assigning, to supply chain components, taggant information that uniquely represent the supply chain components.

FIG. 9 illustrates a non-limiting example of a process for assigning, to supply chain components, combinations of distinct features and taggant fiber counts that uniquely represent the supply chain components, as seen and described above with respect to disclosed embodiments.

Listed below are non-limiting embodiments A1-A24.

A1. Fibers comprising identification fibers, wherein the identification fibers comprise 1 to 100, 1 to 50, 1 to 20, or 1 to 10 chemical markers, wherein an amount of each of the chemical markers, based on a weight of the fibers, is defined as a chemical marker amount, wherein at least one of the chemical marker amounts corresponds to a taggant chemical marker amount, and wherein (i) the chemical markers and (ii) the at least one taggant chemical marker amounts are representative of at least one supply chain component of the fibers.

A2. The fibers of embodiment A1, further comprising standard fibers.

A3. The fibers of any of embodiments A1 or A2, wherein one or more of the chemical markers are selected from the group consisting of one or more taggant non-volatile organic compounds, one or more taggant photoluminescent materials, one or more taggant polymeric additives, one or more taggant carbohydrates, one or more taggant metal oxides, one or more taggant inorganic salts, one or more taggant optical isomers, and one or more taggant isotopically labeled molecules and wherein a number of the taggant chemical marker amounts for each of the chemical makers ranges from 1 to 20.

A4. The fibers of embodiment A3, wherein a number of the taggant non-volatile organic compounds ranges from 1 to 50, 1 to 20, or 1 to 10.

A5. The fibers of embodiment A4, wherein the taggant non-volatile organic compounds comprise fatty acids and wherein the fatty acids comprise lauric acid, palmitic acid, or stearic acid.

A6. The fibers of any of embodiments A3-A5, wherein a number of the taggant photoluminescent materials ranges from 1 to 10 or 1 to 5, wherein the taggant photoluminescent materials comprise phosphorescent quantum dots, and wherein the phosphorescent quantum dots comprise Cd/Se ligand stabilized fluorescent nano-crystals.

A7. The fibers of any of embodiments A3-A6, wherein a number of the taggant polymeric additives ranges from 1 to 20 or 1 to 10 or 1 to 5, wherein the taggant polymeric additives comprise polystyrene, and wherein an average molecular weight of the polystyrene ranges from 500 to 20,000,000, or wherein an average molecular weight of the polystyrene ranges from 500 to 500,000, or wherein an average molecular weight of the polystyrene ranges from 1000 to 100,000.

A8. The fibers of any of embodiments A3-A7, wherein the chemical markers comprise the taggant metal oxides or the taggant inorganic salts, wherein a number of the taggant metal oxides ranges from 1 to 20 or 1 to 10, wherein the taggant metal oxides comprise titanium dioxide, zirconium oxides, zinc oxides, aluminum oxides, manganese oxides, magnesium oxides, calcium oxides, tin oxides, vanadium oxides, nickel oxides or iron oxides, or wherein a number of the taggant inorganic salts ranges from 1 to 20 or 1 to 10, and wherein the taggant inorganic salts comprise salts of cesium, indium, or samarium.

A9. The fibers of any of embodiments A1-A8, wherein an amount of each of the chemical markers ranges from 1 ppb to 10,000 ppm, 100 ppb to 10,000 ppm, or 1 ppm to 2,000 ppm, based on the weight of the fibers.

A10. The fibers of any of embodiments A2-A9, wherein the fibers comprise acrylic, modacrylic, aramid, nylon, polyester, polypropylene, rayon, polyacrylonitrile, polyethylene, PTFE, or cellulose acetate or wherein the identification fibers comprise acrylic, modacrylic, aramid, nylon, polyester, polypropylene, rayon, polyacrylonitrile, polyethylene, PTFE, or cellulose acetate, and the standard fibers comprise cellulose acetate.

A11. The fibers of any of embodiments A1-A10, wherein the at least one supply chain component comprises a manufacturer of the fibers, a manufacture site of the fibers, a manufacturing line of the fibers, a production run of the fibers, a production date of the fibers, a package of the fibers, a warehouse of the fibers, a customer of the fibers, a ship-to location of the fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A12. The fibers of any of embodiments A2-A11, wherein the at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, a ship-to location of the fiber band, a manufacturer of an article comprising the fibers, a manufacture site of the article, a manufacturing line of the article, a production run of the article, a production date of the article, a package of the article, a warehouse of the article, a customer of the article, or a ship-to location of the article.

A13. The fibers of embodiment A12, wherein the at least one supply chain component comprises the manufacturer of the standard fibers and the customer of the standard fibers.

A14. A fiber band comprising the fibers of any of embodiments A1-A13, wherein the fibers comprise cellulose acetate, wherein the fiber band is an acetate tow band, and wherein (i) the chemical markers and (ii) the at least one taggant chemical marker amounts are representative of at least one supply chain component of the acetate tow band.

A15. The fiber band of embodiment A14, wherein the at least one supply chain component comprises the manufacturer of the acetate tow band and the customer of the acetate tow band or wherein the at least one supply chain component comprises the manufacturer of the acetate tow band and the ship-to location of the acetate tow band.

A16. A method for making the fiber band of any of embodiments A14 or A15 wherein the method comprises (a) obtaining the identification fibers; (b) producing the standard fibers on a first fiber production process; and (c) combining the standard fibers with the identification fibers into the acetate tow band, wherein (i) the chemical markers and (ii) the least one taggant chemical marker amounts are representative of at least one supply chain component of the acetate tow band.

A17. The method of embodiment A16, wherein the obtaining of the identification fibers comprises at least one of (i) producing a portion of the identification fibers on the first fiber production process, (ii) producing a portion of the identification fibers on a second fiber production process, or (iii) receiving a portion of the identification fibers from a third party.

A18. The method of any of embodiments A16 or A17, wherein one or more of the chemical markers is added to a spinning solution upstream of the first fiber production process, at a spinning cabinet contained within the first fiber production process, or at an individual spinneret contained within the spinning cabinet.

A19. The method of any of embodiments A16-A18, wherein one or more of the chemical markers are applied to a portion of the identification fibers at any point before the combining of the standard fibers and identification fibers into the acetate tow band.

A20. The method of any of embodiments A16-A19. wherein the method comprises: (a) co-producing the identification fibers and the standard fibers; and (b) combining the identification fibers and the standard fibers into the acetate tow band.

A21. A method for characterizing a fiber sample wherein the fiber sample comprises the fibers of any of embodiments A1-A13 or the fiber band of any of embodiments A14 or A15, wherein the method comprises: (a) dissolving the fiber sample in a solvent to produce a sample solution and/or insolubles; (b) analyzing the sample solution and/or the insoluble to identify the chemical markers and each of the chemical marker amounts.

A22. The method of embodiment A21, further comprising adding N,O-bis(trimethylsilyl)trifluoroacetamide to the sample solution.

A23. The method of any of embodiments A21 or A22, wherein the solvent comprises acetone, tetrahydrofuran, dichloromethane, methanol, chloroform, dioxane, N,N-dimethylformamide, dimethyl sulfoxide, methyl acetate, ethyl acetate, nitric acid or pyridine; or wherein the solvent comprises acetone, tetrahydrofuran, nitric acid, or pyridine.

A24. The method of any of embodiments A21-A23, wherein the analyzing comprises a use of mass spectrometry, spectroscopy, nuclear magnetic resonance, x-ray diffraction, chromatography, gas chromatography coupled to flame ionization detection, size exclusion chromatography followed by UV-vis spectroscopy, fluorescence spectroscopy, inductively coupled plasma (ICP) followed by mass spectrometry, or ICP followed by optical emission spectrometry.

A25. The method of any of embodiments A21-A24, further comprising (a) correlating one or more of the chemical markers and/or taggant chemical marker amounts to a database, wherein the database comprises manufacturer specific taggants; and (b) determining the at least one supply chain component of the fiber sample.

EXAMPLES

Eastman™ Cellulose Acetate for fibers (CA-394-60S) was obtained from Eastman Chemical Company. Acetone (99.7%) was purchased from J. T. Baker. Cesium(I) nitrate (99.9%), indium(III) chloride tetrahytdrate (97%) & samarium(III) chloride hexahydrate (99%) lauric acid (99%), palmitic acid (98%) and stearic acid (97%) methyl laurate (99%), methyl palmitate (99%), methyl stearate (99%) was purchased from Sigma Aldrich. Low polydispersity polystyrene standards with molecular weights of 70,600, 28,500 and 2,400 were purchased from Polymer Laboratories LTD. All materials were used as received. A set of alkyl ligated, Cd/Se ZnS alloyed quantum dots, with emission wavelengths of 490λ, 535λ, 575λ, 630λ & 665λ were purchased from Sigma Aldrich and sourced from Cytodiagnostics Inc. Each 1 mL sample was received as a 1 mg/mL solution and kept under refrigeration until use.

In all of the tables below, spike concentration in ppm is calculated based upon the measured amounts of chemical marker added to the measured amount of cellulose acetate. Recovered concentration in ppm is based upon analytical measurement.

Analytical Methods

Inductively Coupled Plasma Mass Spectrometry (ICP-MS)—Metal concentrations were measured using an Elan 6100 Inductively Coupled Plasma Mass Spectrometer ICP-MS (Perkin Elmer Corp, Norwalk, Conn.). Sample digestion was performed using an UltraWAVE Single Reaction Chamber (SRC) (Milestone, Shelton Conn.) or bulk digestions in $HNO_3$ on a hotplate. Samples were prepared by weighing ~0.25 g into a cleaned quartz tube, 4 ml $HNO_3$ was then added and the tube was capped and digested using a pre-programmed set of conditions. Bulk digestion was carried out on a 1 gram film sample, transferred into a 150 mL quartz beaker to which 10 mL of $HNO_3$ acid was added and heated on a hot plate for 2 hrs at 200° C. or until the sample had completely digested. Once digested the sample was quantitatively transferred to a 100 mL volumetric flask and diluted with $HNO_3$. Samples were then quantitatively transferred to a 25 mL volumetric flask using Millipore water. A Rubidium internal standard was added and the samples were analyzed by ICP-MS. The ICP-MS was calibrated at 5 part per billion using matrix matched standards prepared from certified calibration standards purchased from High Purity Standards (Charleston, S.C.). The calibrated masses were samarium—151.92, cesium—132.905 and indium—114.904.

Gas Chromatography-Flame Ionization Detection (GC-FID)—The concentration of taggant fatty acid in cellulose acetate (CA) was determined via an internal standard-based, gas chromatography method. A Shimadzu 2010 gas chromatograph with CombiPAL autosampler and flame ionization detector (FID) was utilized; a DB-5 (30 m×0.32 mm×0.25 μm) capillary column was used. Samples were prepared by weighing ~0.05 g of tagged CA into a 2 mL glass GC vial; 500 μL of internal standard solution (0.1% (w/v) dodecane in pyridine) was then added to the vial using an eVol digital pipette equipped with a 500 μL tip. Samples were then heated at 80° C. for ten minutes. After heating, 1.00 mL of N,O-Bis(trimethylsilyl)trifluoroacetamide (BSTFA) was added to derivatize the fatty acid taggant. Samples were heated at 80° C. for five minutes, vortexed, then heated at 80° C. for 25 minutes. The samples were subsequently centrifuged at 5,000 rpm for 10 minutes (VWR Clinical 200); the supernatant was subsequently transferred to a second GC vial containing a 300 μL glass insert.

Gel Permeation Chromatography with UV Detection—An Agilent series 1100 liquid chromatographic instrument was used. The instrument consists of a degasser, an isocratic pump, an auto-sampler, a column oven, a refractive index detector and a UV/VIS detector. The column set consisted of Agilent PLgel 5 micron guard, Mixed-C and Oligopore columns in series. The solvent used to dissolve the samples and as the eluent for the system was stabilized tetrahydrofuran. The flow rate for the system was set at 1.0 ml/min. The auto-sampler used an injection volume of 50 μl. The column oven was set at 30° C. The refractive index detector was set at 30° C. The UV/VIS detector was set at 260 nm for detection purposes. The instrument was calibrated using a set of 14 mono-disperse polystyrene standards ranging from 3,220,000 to 580 molecular weight and a 162 molecular weight phenyl hexane.

Fluorescence Spectroscopy—All samples were stored in a dark refrigerator until the spectra were acquired. The fluorescence spectra were collected using a Horiba Fluorolog®-3-22 Spectrofluorometer. Samples were placed in quartz fluorescence cells and excited at 295 nm with the emission recorded from 200 nm to 800 nm. All slits were set to 1 nm and a 0.1 s integration time was used. All data is reported normalized by the lamp intensity at the time of measurement in CPS/microamps.

Example 1

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of cesium (I) nitrate (0.68 mg/mL in cesium), prepared in a 9:1 acetone/water solution, and was added to the mixture to give a dope that was 68 ppm in cesium based on total solids. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for ICP-MS analysis. The calculated spiked concentration of cesium, the measured concentration of cesium and the Recovery calculated as the percent measured divided by spiked are given in Table 1. All metal concentrations are based on metal alone.

Examples 2-5

Example 1 was repeated to prepare four additional films, by linearly increasing the concentration by a factor of two in each film. The results are summarized in Table 1.

Example 6

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of indium(III) chloride tetrahydrate (0.39 mg/mL in indium), prepared in a 9:1 acetone/water solution, and was added to the mixture to give a dope that was 39 ppm in Indium based on total solids. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to further dry under the draft of the fume hood for 1 hr. The samples were then removed from the dishes and submitted for ICP-MS analysis. The calculated spiked concentration of indium, the measured concentration of indium, and the % Recovery calculated as the percent measured divided by spiked are given in Table 1.

Examples 7-10

Example 6 was repeated to prepare four additional films, by linearly increasing the concentration by a factor of two in each film. The results are summarized in Table 1 including the spiked and recovered amounts and percent recovery.

Example 11

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of samarium(III) chloride hexahydrate (0.41 mg/mL in samarium), prepared in a 9:1 acetone/water solution, and was added to the mixture to give a dope that was 41 ppm in samarium based on total solids. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to further dry under the draft of the fume hood for 1 hr. The samples were then removed from the dishes and submitted for ICP-MS analysis. The calculated spiked concentration of samarium, the measured concentration of samarium and the % Recovery calculated as the percent measured divided by spiked are given in Table 1.

Examples 12-15

Example 11 was repeated to prepare four additional films, by linearly increasing the concentration by a factor of two in each film. The results are summarized in Table 1.

TABLE 1

Examples of Metal Recovered Cellulose Acetate Films

| Example | Metal | Spiked Conc. (ppm) | Recovered Conc. (ppm) | % Recovery |
|---|---|---|---|---|
| 1 | Cesium | 68 | 54 | 79 |
| 2 | Cesium | 136 | 109 | 80 |
| 3 | Cesium | 204 | 169 | 83 |
| 4 | Cesium | 272 | 265 | 97 |
| 5 | Cesium | 340 | 285 | 84 |
| 6 | Indium | 39 | 30 | 77 |
| 7 | Indium | 78 | 65 | 83 |
| 8 | Indium | 117 | 96 | 82 |
| 9 | Indium | 156 | 129 | 83 |
| 10 | Indium | 195 | 166 | 85 |
| 11 | Samarium | 41 | 35 | 85 |
| 12 | Samarium | 82 | 63 | 77 |
| 13 | Samarium | 123 | 96 | 78 |
| 14 | Samarium | 164 | 140 | 85 |
| 15 | Samarium | 205 | 175 | 85 |

Example 16

A 20 mL scintillation vial was charged with cellulose acetate (1.00 g) followed by HPLC grade acetone (11.38 mL) to give a mixture 10% (w/w) in solids. 300 µL of a 1.0 mg/mL stock solution of samarium(III) chloride hexahydrate (0.41 mg/mL in samarium) stock solution, 100 µL of a 1.0 mg/mL stock solution of cesium(I) nitrate (0.68 mg/mL in cesium) stock solution and 200 µL of a 1.0 mg/mL stock solution of indium(III) chloride tetrahydrate (0.39 mg/mL in Indium) was added to the mixture to give a dope that was 123 ppm in samarium, 68 ppm in cesium, and 78 ppm in indium, respectively, based on polymer solids. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to further dry under the draft of the fume hood for 1 hr. The samples were then removed from the dishes and submitted for ICP-MS analysis. The calculated spiked concentration of samarium, cesium and indium, the measured concentration of samarium, cesium and indium, and the % Recovery calculated as the percent measured divided by spiked are given in Table 2.

Examples 17-19

Example 16 was repeated to prepare three additional films with varying amounts of each metal. The results are summarized in Table 2.

TABLE 2

Examples of Cellulose Acetate Films Containing Multiple Metals

| | Spiked Conc.(ppm) | | | Recovered Conc.(ppm) | | |
|---|---|---|---|---|---|---|
| Example | Samarium | Cesium | Indium | Samarium | Cesium | Indium |
| 16 | 123 | 68 | 78 | 107 | 56 | 66 |
| 17 | 82 | 272 | 117 | 66 | 232 | 103 |
| 18 | 41 | 204 | 195 | 33 | 167 | 168 |
| 19 | 205 | 136 | 156 | 178 | 113 | 140 |

Examples 16-19 demonstrate that metal salts can be used as chemical taggants and that different amounts of the metal salts can be detected and use in a code for tracking and tracing material through the supply chain.

Example 20

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of lauric acid, prepared in acetone, was added to the mixture to give a dope that was 100 ppm in lauric acid based on total solids. GC analysis of this stock solution reported the true concentration to be 0.908 g/mL. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for GC-FID analysis. All samples were prepared in duplicate. The levels of chemical taggant are reported as the average value with error bars corresponding to (+/−) one standard deviation.

Examples 21-24

Example 20 was repeated to prepare four additional films, by linearly increasing the concentration in increments of 100 ppm in each film. The results are summarized in Table 3.

Example 25

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of palmitic acid, prepared in acetone, was added to the mixture to give a dope that was 100 ppm in palmitic acid based on total solids. GC analysis of this stock solution reported the true concentration to be 1.10 g/mL. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for GC-FID analysis. All samples were prepared in duplicate and the results are given in Table 3.

Examples 26-29

Example 25 was repeated to prepare four additional films, by linearly increasing the concentration in increments of 100 ppm in each film. The results are summarized in Table 3.

Example 30

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of stearic acid, prepared in acetone, was added to the mixture to give a dope that was 100 ppm in stearic acid based on total solids. GC analysis of this stock solution reported the true concentration to be 0.888 g/mL. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for GC-FID analysis. All samples were prepared in duplicate and the results are given in Table 3.

Examples 31-34

Example 30 was repeated to prepare four additional films, by linearly increasing the concentration in increments of 100 ppm in each film. The results are summarized in Table 3 including the spiked and recovered concentration of stearic acid and percent recovery.

TABLE 3

Examples of Fatty Acid Spiked Cellulose Acetate Films

| | | | Duplicate Samples | | |
|---|---|---|---|---|---|
| Example | Fatty Acid | Spiked Conc. (ppm) | Recovered Conc. (ppm) | Recovered Conc. (ppm) | Average % Recovery |
| 20 | Lauric | 91 | 71 | 91 | 81 |
| 21 | Lauric | 182 | 173 | 172 | 86 |
| 22 | Lauric | 272 | 275 | 263 | 90 |
| 23 | Lauric | 363 | 361 | 376 | 92 |
| 24 | Lauric | 454 | 450 | 464 | 91 |
| 25 | Palmitic | 110 | 111 | 101 | 106 |
| 26 | Palmitic | 220 | 212 | 213 | 106 |
| 27 | Palmitic | 330 | 337 | 323 | 110 |
| 28 | Palmitic | 440 | 462 | 424 | 110 |
| 29 | Palmitic | 550 | 630 | 536 | 116 |
| 30 | Stearic | 89 | 91 | 100 | 96 |
| 31 | Stearic | 178 | 180 | 233 | 103 |

TABLE 3-continued

Examples of Fatty Acid Spiked Cellulose Acetate Films

| | | | Duplicate Samples | | |
|---|---|---|---|---|---|
| Example | Fatty Acid | Spiked Conc. (ppm) | Recovered Conc. (ppm) | Recovered Conc. (ppm) | Average % Recovery |
| 32 | Stearic | 266 | 270 | 274 | 91 |
| 33 | Stearic | 355 | 365 | 371 | 92 |
| 34 | Stearic | 444 | 449 | 435 | 88 |

Examples 35-38

The procedure of Example 20 was repeated to prepare four additional films, comprising varying concentrations of lauric acid, palmitic acid, and stearic acid. The results are summarized in Table 4 including the spiked and recovered concentrations of each fatty acid and percent recovery.

TABLE 4

Examples of Cellulose Acetate Films Containing Multiple Fatty Acids

| | Spiked Conc. (ppm) | | | Duplicate Samples | | | | | | Average % Recovery | | |
|---|---|---|---|---|---|---|---|---|---|---|---|---|
| | | | | Recovered Conc. (ppm) | | | Recovered Conc. (ppm) | | | | | |
| Example | Lauric | Palmitic | Stearic | Lauric | Palmitic | Stearic | Lauric | Palmitic | Stearic | Lauric | Palmitic | Stearic |
| 35 | 182 | 330 | 444 | 162 | 294 | 385 | 171 | 302 | 413 | 92 | 90 | 90 |
| 36 | 363 | 330 | 178 | 327 | 286 | 164 | 326 | 305 | 163 | 90 | 90 | 92 |
| 37 | 272 | 550 | 89 | 251 | 513 | 90 | 253 | 535 | 91 | 93 | 95 | 102 |
| 38 | 454 | 220 | 355 | 425 | 212 | 334 | 478 | 229 | 374 | 99 | 100 | 100 |

Example 39

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of methyl laurate, prepared in acetone, was added to the mixture to give a dope that was 100 ppm in methyl laurate based on total solids. GC analysis of this stock solution reported the true concentration to be 1.22 g/mL. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for GC-FID analysis. All samples were prepared in duplicate and the results are summarized in Table 5.

Examples 40-43

Example 39 was repeated to prepare four additional films, by linearly increasing the concentration in increments of 100 ppm in each film. The results are summarized in Table 5.

Example 44

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of methyl palmitate, prepared in acetone, was added to the mixture to give a dope that was 100 ppm in methyl palmitate based on total solids. GC analysis of this stock solution reported the true concentration to be 1.37 g/mL. The vial was then placed on a continuous roller for a minimum of 16 hours or until a homogenous dope was formed. The dope was then poured into labeled culture dish bottoms (100 mm×20 mm) set in a transparent container with a cover. The solvent was allowed to slowly evaporate under cover for 5 hrs. The cover was then removed and the samples allowed to dry further under the draft of the fume hood for 1 hr. The samples were then removed from the dishes and submitted for GC-FID analysis. All samples were prepared in duplicate. The results are summarized in Table 5.

Examples 45-48

Example 44 was repeated to prepare four additional films, by linearly increasing the concentration in increments of 100 ppm in each film. The results are summarized in Table 5.

TABLE 5

Examples of Fatty Acid Methyl Ester Recovered Film Samples

| | | | Duplicate Samples | | |
|---|---|---|---|---|---|
| Sample | FAME | Spiked Conc. (ppm) | Recovered Conc. (ppm) | Recovered Conc. (ppm) | Average % Recovery |
| 39 | Methyl Laurate | 122 | 95 | 93 | 77 |
| 40 | Methyl Laurate | 244 | 173 | 185 | 73 |
| 41 | Methyl Laurate | 366 | 293 | 277 | 77 |
| 42 | Methyl Laurate | 488 | 401 | 390 | 81 |
| 43 | Methyl Laurate | 610 | 477 | 489 | 79 |
| 44 | Methyl Palmitate | 133 | 108 | 110 | 81 |
| 45 | Methyl Palmitate | 266 | 208 | 232 | 82 |
| 46 | Methyl Palmitate | 399 | 334 | 354 | 86 |
| 47 | Methyl Palmitate | 532 | 452 | 425 | 82 |
| 48 | Methyl Palmitate | 665 | 553 | 575 | 84 |

The fatty acid methyl ester average percent recovery was lower than what was seen in the fatty acids. As only a part of each film was digested and tested, dope samples were made and tested directly to rule out variability in concentration throughout the film.

Example 49

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of methyl palmitate, prepared in acetone, was added to the mixture to give a dope that was 100 ppm in methyl palmitate based on total solids. GC analysis of this stock solution reported the true concentration to be 1.33 g/mL. The vial was then placed on a continuous roller for a minimum of 16 hours or until a homogenous dope was formed. The samples were then submitted for GC-FID analysis. All samples were prepared in duplicate and the results are summarized in Table 6.

Examples 50-53

Example 49 was repeated to prepare four additional dopes, by linearly increasing the concentration in increments of 100 ppm in each dope. The results are summarized in Table 6.

Example 54

A 20 mL scintillation vial was charged with cellulose acetate (1.00 g) followed by HPLC grade acetone (11.38 mL) to give a mixture 10% (w/w) in solids. 100 µL of a 1.0 mg/mL stock solution of methyl stearate, prepared in acetone, was added to the mixture to give a dope that was 100 ppm in methyl stearate based on total solids. GC analysis of this stock solution reported the true concentration to be 1.03 g/mL. The vial was then placed on a continuous roller for a minimum of 16 hours or until a homogenous dope was formed. The samples were then submitted for GC-FID analysis. All samples were prepared in duplicate and the results are summarized in Table 6.

Examples 55-58

Example 54 was repeated to prepare four additional dopes, by linearly increasing the concentration in increments of 100 ppm in each dope. The results are summarized in Table 6.

TABLE 6

Examples of Fatty Acid Methyl Ester Recovered Dope Samples

| Sample | FAME | Spiked Conc. (ppm) | Duplicate Samples Recovered Conc. (ppm) | Recovered Conc. (ppm) | Average % Recovery |
|---|---|---|---|---|---|
| 49 | Methyl Palmitate | 10 | 7 | 7 | 68 |
| 50 | Methyl Palmitate | 20 | 17 | 15 | 82 |
| 51 | Methyl Palmitate | 29 | 31 | 30 | 105 |
| 52 | Methyl Palmitate | 39 | 38 | 39 | 98 |
| 53 | Methyl Palmitate | 48 | 48 | 51 | 103 |
| 54 | Methyl Stearate | 10 | 12 | 12 | 121 |
| 55 | Methyl Stearate | 20 | 20 | 19 | 98 |
| 56 | Methyl Stearate | 29 | 27 | 30 | 98 |
| 57 | Methyl Stearate | 39 | 40 | 40 | 102 |
| 58 | Methyl Stearate | 48 | 48 | 45 | 97 |

Pilot scale evaluations of methyl laurate, methyl palmitate, and methyl stearate were conducted in a similar manner as the fatty acid examples described below. The recovery of the fatty acid methyl esters was far below expectation. Without being bound by any theory, we hypothesize that the fatty acid methyl esters were poorly compatible with the CA polymer and had a greater affinity for the evaporating acetone during spinning, despite their relatively high boiling points and low vapor pressures. No further work on the fatty acid methyl esters as chemical markers for inclusion with cellulose acetate was performed.

Pilot Scale Evaluation of Fatty Acids as Chemical Taggants

Fatty acids were used to produce a series of tagged cellulose acetate threads on pilot plant equipment, each production run made 1,700 denier threads. The spooled threads, containing known concentrations of each fatty acid, were then combined in a modular fashion with cellulose acetate threads without any fatty acid, to produce an encoded cellulose acetate tow band having a denier of 34,000. The band of acetate tow was then formed into filter rods using industry standard equipment with the addition of a plasticizer common to the industry.

The taggant threads were made by first preparing a cellulose acetate dope concentrate that contained 907 g of fatty acid, cellulose acetate, a pigment (Copper Phthalocyanine, CAS No. 147-14-8) to aid in tracking of the additive dope through the process and acetone, to create a dope containing 28.3% solids. This dope concentrate had a target concentration of 51819 ppm in fatty acid. This dope concentrate was then metered into virgin cellulose acetate dope through a controlled additive system and homogenized using an in-line mixing system. The mixed dope was then fed through a spinning cabinet and treated with lubricant, familiar to those skilled in the art and the resultant thread collected onto spools. The system was purged with virgin cellulose acetate dope before moving to the subsequent taggant mixture. The target concentration of fatty acid in the tagged thread was 4000 ppm. Approximately 15-20 spools of thread were generated during the spinning of a single taggant batch. Three sets of tagged spools were made in this fashion that contained lauric, palmitic and stearic acids.

Examples 59-109

To ensure uniformity of the taggant concentration along the length of the thread, samples were removed from each spool in each set of fatty acid threads and analyzed via GC using FID detection as previous described. The order of the examples does not represent the order in which each spool was produced. The results are summarized in Table 7 including individual and global taggant averages, standard deviations and percent relative standard deviations.

TABLE 7

Examples of Fatty Acid Recovered Cellulose Acetate Thread

| Example | Fatty Acid | Recovered Conc. (ppm) | | |
|---|---|---|---|---|
| 59 | Lauric | 4002 | | |
| 60 | Lauric | 3685 | | |
| 61 | Lauric | 4249 | | |
| 62 | Lauric | 4321 | | |
| 63 | Lauric | 4216 | | |
| 64 | Lauric | 4444 | | |
| 65 | Lauric | 4120 | | |
| 66 | Lauric | 4076 | Average | 4230 |
| 67 | Lauric | 4344 | STDEV | 195 |
| 68 | Lauric | 4513 | % RSD | 4.61 |
| 69 | Lauric | 4366 | % Recovery | 105.75 |
| 70 | Lauric | 4399 | | |
| 71 | Lauric | 4129 | | |
| 72 | Lauric | 4200 | | |
| 73 | Lauric | 4277 | | |
| 74 | Lauric | 4212 | | |
| 75 | Lauric | 4356 | | |
| 76 | Palmitic | 4455 | | |
| 77 | Palmitic | 4177 | | |
| 78 | Palmitic | 4464 | | |
| 79 | Palmitic | 4424 | | |
| 80 | Palmitic | 4442 | | |
| 81 | Palmitic | 4120 | | |
| 82 | Palmitic | 4010 | | |
| 83 | Palmitic | 4231 | Average | 4215 |
| 84 | Palmitic | 4434 | STDEV | 236 |

TABLE 7-continued

Examples of Fatty Acid Recovered Cellulose Acetate Thread

| Example | Fatty Acid | Recovered Conc. (ppm) | | |
|---|---|---|---|---|
| 85 | Palmitic | 4430 | % RSD | 5.60 |
| 86 | Palmitic | 4194 | % Recovery | 105.38 |
| 87 | Palmitic | 3700 | | |
| 88 | Palmitic | 1636* | | |
| 89 | Palmitic | 4145 | | |
| 90 | Palmitic | 4197 | | |
| 91 | Palmitic | 4256 | | |
| 92 | Palmitic | 3766 | | |
| 93 | Stearic | 4305 | | |
| 94 | Stearic | 4435 | | |
| 95 | Stearic | 4267 | | |
| 96 | Stearic | 4004 | | |
| 97 | Stearic | 4102 | | |
| 98 | Stearic | 3990 | | |
| 99 | Stearic | 4143 | | |
| 100 | Stearic | 4174 | Average | 4085 |
| 101 | Stearic | 4077 | STDEV | 166 |
| 102 | Stearic | 4100 | % RSD | 4.08 |
| 103 | Stearic | 4223 | % Recovery | 102.13 |
| 104 | Stearic | 3895 | | |
| 105 | Stearic | 3910 | | |
| 106 | Stearic | 4098 | | |
| 107 | Stearic | 3925 | | |
| 108 | Stearic | 4013 | | |
| 109 | Stearic | 3777 | | |
| | | | Global Average | 4151 |
| | | | Global STDEV | 196 |
| | | | Global % RSD | 4.72 |
| | | | Global % Recovery | 103.78 |

*Example 88 is believed to represent an anomaly where system contamination from the previous fatty acid in the mixing system had occurred. This data point was excluded from the statistical treatment since this type of error was a result of a correctable system contamination and not a reflection of the method reliability.

Tagged spools, in addition to un-tagged spools, were then loaded onto a device to allow the pilot-scale manufacture of a band of acetate tow. Through the addition or subtraction of a defined number of spools of a particular taggant type, the final concentration and taggant makeup in the tow band could be altered. The collected tow band was pressed into a bale and subsequently used in the manufacture of the filter rods. The filter rods were made on AF2/KDF2 plugmaker at 400 m/min. The filter rod length was 120 mm and circumference was 24.4 mm. Samples from the manufactured filter rods were prepared for GC analysis in the same manner as previously described. Each of the examples below represent analysis of a single filter rod from the batch of filter rods produced, taken in no particular order. The code notation for the filter rod samples correspond to the spike concentration (ppm), in the filter rod and based on the weight of cellulose acetate, of each fatty acid in the order, lauric acid, palmitic acid, and stearic acid.

Examples 110-127

The spike concentration for lauric acid, palmitic acid, and stearic acid in Examples 110-127 were 1000-000-000. The results are summarized in Table 8.

TABLE 8

Examples of Fatty Acid Encoded Cellulose Acetate Filter Rods (Code 1000-000-000)

| | Recovered Conc. (ppm) | | |
|---|---|---|---|
| Example | Lauric Acid | Palmitic Acid | Stearic Acid |
| 110 | 935 | 0 | 0 |
| 111 | 1042 | 0 | 0 |
| 112 | 956 | 0 | 0 |
| 113 | 926 | 0 | 0 |
| 114 | 1127 | 0 | 0 |
| 115 | 952 | 0 | 0 |
| 116 | 1078 | 0 | 0 |
| 117 | 969 | 0 | 0 |
| 118 | 948 | 0 | 0 |
| 119 | 1042 | 0 | 0 |
| 120 | 1153 | 0 | 0 |
| 121 | 1121 | 0 | 0 |
| 122 | 1162 | 0 | 0 |
| 123 | 1140 | 0 | 0 |
| 124 | 1167 | 0 | 0 |
| 125 | 1177 | 0 | 0 |
| 126 | 1174 | 0 | 0 |
| 127 | 1128 | 0 | 0 |
| Average | 1066 | 0 | 0 |
| Std. Dev. | 92 | 0 | 0 |
| Average % Recovery | 107 | N/A | N/A |

Examples 128-145

The spike concentration for lauric acid, palmitic acid, and stearic acid in Examples 128-145 were 000-1000-000. Filter rods were prepared in the same manner as described above. The results are summarized in Table 9.

TABLE 9

Examples of Fatty Acid Encoded Cellulose Acetate Filter Rods (Code 000-1000-000)

| | Recovered Conc. (ppm) | | |
|---|---|---|---|
| Example | Lauric Acid | Palmitic Acid | Stearic Acid |
| 128 | 0 | 1083 | 0 |
| 129 | 0 | 848 | 0 |
| 130 | 0 | 1112 | 0 |
| 131 | 0 | 1060 | 0 |
| 132 | 0 | 813 | 0 |
| 133 | 0 | 846 | 0 |
| 134 | 0 | 1042 | 0 |
| 135 | 0 | 1011 | 0 |
| 136 | 0 | 965 | 0 |
| 137 | 0 | 903 | 0 |
| 138 | 0 | 1142 | 0 |
| 139 | 0 | 1207 | 0 |
| 140 | 0 | 1140 | 0 |
| 141 | 0 | 1333 | 0 |
| 142 | 0 | 1046 | 0 |
| 143 | 0 | 1123 | 0 |
| 144 | 0 | 1028 | 0 |
| 145 | 0 | 1114 | 0 |
| Average | 0 | 1045 | 0 |
| Std. Dev. | 0 | 130 | 0 |
| Average % Recovery | N/A | 105 | N/A |

Examples 146-163

The spike concentration for lauric acid, palmitic acid, and stearic acid in Examples 146-163 were 000-000-1000. Filter rods were prepared in the same manner as described above.

The results are summarized in Table 10 including the spiked and recovered amounts and percent recovery.

TABLE 10

Examples of Fatty Acid Encoded Cellulose Acetate Filter Rods (Code 000-000-1000)

| | Recovered Conc. (ppm) | | |
|---|---|---|---|
| Example | Lauric Acid | Palmitic Acid | Stearic Acid |
| 146 | 0 | 0 | 966 |
| 147 | 0 | 0 | 921 |
| 148 | 0 | 0 | 942 |
| 149 | 0 | 0 | 1001 |
| 150 | 0 | 0 | 911 |
| 151 | 0 | 0 | 965 |
| 152 | 0 | 0 | 965 |
| 153 | 0 | 0 | 988 |
| 154 | 0 | 0 | 923 |
| 155 | 0 | 0 | 1089 |
| 156 | 0 | 0 | 1027 |
| 157 | 0 | 0 | 1079 |
| 158 | 0 | 0 | 1114 |
| 159 | 0 | 0 | 961 |
| 160 | 0 | 0 | 1002 |
| 161 | 0 | 0 | 866 |
| 162 | 0 | 0 | 1080 |
| 163 | 0 | 0 | 959 |
| Average | 0 | 0 | 987 |
| Std. Dev. | 0 | 0 | 66 |
| Average % Recovery | N/A | N/A | 99 |

Examples 164-181

The spike concentration for lauric acid, palmitic acid, and stearic acid in Examples 164-181 were 600-800-1000. Filter rods were prepared in the same manner as described above. The results are summarized in Table 11.

TABLE 11

Examples of Fatty Acid Encoded Cellulose Acetate Filter Rods (Code 600-800-1000)

| | Recovered Conc. (ppm) | | |
|---|---|---|---|
| Example | Lauric Acid | Palmitic Acid | Stearic Acid |
| 164 | 593 | 839 | 1091 |
| 165 | 570 | 839 | 1115 |
| 166 | 612 | 892 | 1232 |
| 167 | 571 | 896 | 1271 |
| 168 | 589 | 868 | 1253 |
| 169 | 688 | 995 | 1312 |
| 170 | 618 | 802 | 990 |
| 171 | 563 | 803 | 1170 |
| 172 | 545 | 756 | 984 |
| 173 | 652 | 962 | 1440 |
| 174 | 703 | 1134 | 1519 |
| 175 | 624 | 888 | 1325 |
| 176 | 612 | 792 | 1120 |
| 177 | 642 | 811 | 1017 |
| 178 | 744 | 1021 | 1294 |
| 179 | 772 | 1061 | 1393 |
| 180 | 795 | 1052 | 1256 |
| 181 | 716 | 932 | 1183 |
| Average | 645 | 908 | 1220 |
| Std. Dev. | 73 | 105 | 147 |
| Average % Recovery | 107 | 113 | 122 |

Examples 182-199

The spike concentration for lauric acid, palmitic acid, and stearic acid in Examples 182-199 were 800-1000-600. Filter rods were prepared in the same manner as described above. The results are summarized in Table 12.

TABLE 12

Examples of Fatty Acid Encoded Cellulose Acetate Filter Rods (Code 800-1000-600)

| | Recovered Conc. (ppm) | | |
|---|---|---|---|
| Example | Lauric Acid | Palmitic Acid | Stearic Acid |
| 182 | 858 | 1025 | 668 |
| 183 | 859 | 904 | 594 |
| 184 | 878 | 987 | 590 |
| 185 | 854 | 1081 | 702 |
| 186 | 773 | 968 | 680 |
| 187 | 745 | 855 | 604 |
| 188 | 811 | 914 | 612 |
| 189 | 840 | 1021 | 698 |
| 190 | 791 | 949 | 640 |
| 191 | 950 | 1232 | 858 |
| 192 | 894 | 1314 | 851 |
| 193 | 865 | 1006 | 724 |
| 194 | 974 | 1014 | 657 |
| 195 | 783 | 1011 | 672 |
| 196 | 897 | 1049 | 759 |
| 197 | 825 | 1029 | 763 |
| 198 | 857 | 977 | 665 |
| 199 | 968 | 1122 | 687 |
| Average | 857 | 1025 | 690 |
| Std. Dev. | 63 | 108 | 76 |
| Average % Recovery | 107 | 103 | 115 |

Examples 200-217

The spike concentration for lauric acid, palmitic acid, and stearic acid in Examples 200-217 were 1000-600-800. Filter rods were prepared in the same manner as described above. The results are summarized in Table 13.

TABLE 13

Examples of Fatty Acid Encoded Cellulose Acetate Filter Rods (Code 800-1000-600)

| | Recovered Conc. (ppm) | | |
|---|---|---|---|
| Example | Lauric Acid | Palmitic Acid | Stearic Acid |
| 200 | 897 | 570 | 887 |
| 201 | 862 | 558 | 840 |
| 202 | 894 | 616 | 988 |
| 203 | 915 | 520 | 851 |
| 204 | 912 | 624 | 925 |
| 205 | 891 | 520 | 792 |
| 206 | 960 | 634 | 972 |
| 207 | 987 | 695 | 1098 |
| 208 | 941 | 718 | 1098 |
| 209 | 1142 | 723 | 1173 |
| 210 | 1012 | 637 | 858 |
| 211 | 1084 | 648 | 1059 |
| 212 | 1141 | 766 | 1091 |
| 213 | 1074 | 672 | 913 |
| 214 | 1051 | 606 | 882 |

TABLE 13-continued

Examples of Fatty Acid Encoded Cellulose
Acetate Filter Rods (Code 800-1000-600)

| Example | Recovered Conc. (ppm) | | |
|---|---|---|---|
| | Lauric Acid | Palmitic Acid | Stearic Acid |
| 215 | 1085 | 684 | 1035 |
| 216 | 1158 | 556 | 869 |
| 217 | 1198 | 702 | 1005 |
| Average | 1011 | 636 | 963 |
| Std. Dev. | 105 | 70 | 107 |
| Average % Recovery | 101 | 106 | 120 |

A series of polyethylene glycols (PEG's) as chemical taggants in cellulose acetate were evaluated using size exclusion chromatography as the method of separation and refractive index (RI) as the method of detection. The PEG's ranged in molecular weight from 200 to 20,000. Initial screening showed poor solubility of PEG's greater than 2,000 in solvents suitable for analysis (tetrahydrofuran, methylene chloride and hexafluoroisopropanol). Poor resolution of the lower molecular weight PEG fragments using these same solvents. No further work on using PEG's as a chemical taggant for acetate tow was pursued.

Polystyrenes are soluble in a broad range of solvents; including acetone and have the advantage of an aromatic side group which allows for detection via UV-Vis. Detection via UV-Vis simplifies analysis since cellulose acetate has a low UV response at the selected wavelengths, which makes the cellulose acetate almost invisible. To determine the linearity of signal intensity with increasing polystyrene concentration, calibration standards in THF were prepared for each polystyrene standard at 20, 30, 40, 50, and 100 ppm. These solutions were analyzed GPC with UV-Vis detection. Within this concentration range, signal intensity increased in a linear fashion with an increase in concentration with $R^2$ values near unity.

Example 218

A cellulose acetate dope containing polystyrene taggant was made by adding 2.0 mL of the respective calibration standard solution to a vial followed by enough cellulose acetate powder to provide the desired concentration of polystyrene. The vial was then placed on a shaker apparatus and gently agitated for more than 16 hrs. The homogenous dopes were then then analyzed via GPC with UV detection at 260 nm.

Examples 219-232

Example 218 was repeated to prepare additional dopes, for each polystyrene oligomer, by linearly increasing the concentration in increments of 10 ppm in each dope up to 50 ppm and a terminal sample at 100 ppm. The results are summarized in Table 14 including the spiked and recovered amounts and percent recovery.

TABLE 14

Examples of Polystyrene Spiked Cellulose Acetate Dope Samples

| | | | Duplicate Samples | | |
|---|---|---|---|---|---|
| Sample | Polystyrene Std. | Spiked Conc. (ppm) | Recovered Conc. (ppm) | Recovered Conc. (ppm) | Average % Recovery |
| 218 | 2k | 20 | 19 | 20 | 96 |
| 219 | 2k | 30 | 28 | 30 | 96 |
| 220 | 2k | 40 | 38 | 40 | 98 |
| 221 | 2k | 50 | 46 | 49 | 94 |
| 222 | 2k | 100 | 98 | 107 | 102 |
| 223 | 20K | 20 | 21 | 22 | 109 |
| 224 | 20K | 30 | 29 | 30 | 99 |
| 225 | 20K | 40 | 39 | 41 | 100 |
| 226 | 20K | 50 | 49 | 52 | 101 |
| 227 | 20K | 100 | 97 | 102 | 100 |
| 228 | 70k | 20 | 20 | 22 | 104 |
| 229 | 70k | 30 | 29 | 31 | 101 |
| 230 | 70k | 40 | 39 | 41 | 100 |
| 231 | 70k | 50 | 49 | 51 | 100 |
| 232 | 70k | 100 | 97 | 103 | 100 |

Examples 233-235

The procedure of Example 218 was repeated to prepare three additional dopes, with varying concentrations of all polystyrene standards. The results are summarized in Table 15.

TABLE 15

Examples of Polystyrene Oligomer Encoded Cellulose Acetate Dopes

| | Spiked Conc. (ppm) | | | Duplicate Samples | | | | | | | | |
|---|---|---|---|---|---|---|---|---|---|---|---|---|
| | | | | Recovered Conc. (ppm) | | | Recovered Conc. (ppm) | | | Average % Recovery | | |
| Example | 2,000 MW | 20,000 MW | 70,000 MW | 2,000 MW | 20,000 MW | 70,000 MW | 2,000 MW | 20,000 MW | 70,000 MW | 2,000 MW | 20,000 MW | 70,000 MW |
| 233 | 100 | 20 | 50 | 93 | 23 | 53 | 91 | 23 | 52 | 92 | 114 | 106 |
| 234 | 20 | 50 | 100 | 16 | 49 | 97 | 17 | 49 | 98 | 83 | 98 | 98 |
| 235 | 50 | 100 | 20 | 42 | 88 | 20 | 43 | 88 | 20 | 85 | 88 | 100 |

To determine the linearity of signal intensity with increasing alkylated Cd/Se nanocrystals concentration, calibration standards were prepared for alkylated Cd/Se nanocrystals of each emission wavelength (490, 525, 575, 630 & 665 nm) in a solution of 230 mg of cellulose acetate in THF. Solutions were prepared at 10 ppm, 8 ppm, 6 ppm, 4 ppm and 2 ppm such that each solution was 5% wt. solids starting from a 100 ppm stock solutions of each Cd/Se nanocrystal in THF. These solutions were then analyzed via fluorescence spectroscopy. Within this concentration range, signal intensity increased in a linear fashion with an increase in concentration with $R^2$ values ranging from 0.95-0.99.

Examples 236-239

A speed mixing cup is charged with 1.0 g of cellulose acetate and 14.46 mL of THF. The container is sealed and placed on a continuous roller overnight to give a homogenous dope. Using the previously prepared 100 ppm stock solutions, varying concentrations of 525, 575 and 635 nm Cd/Se nanocrystal were then added to the prepared dopes in a manner so that all samples were 5% wt. in solids. The containers were then sealed and placed in a speed mixer for 60 sec. at 3500 rpm. The finished dopes were then transferred to quartz cuvettes for analysis via fluorescence spectroscopy. The results are summarized in Table 16 including the spiked and recovered amounts and percent recovery.

TABLE 16

Examples of Polystyrene Oligomer Encoded Cellulose Acetate Dopes

| Example | Recovered Conc. (ppm) | | | Recovered Conc. (ppm) | | | % Recovery | | |
|---|---|---|---|---|---|---|---|---|---|
| | 525 nm | 575 nm | 665 nm | 525 nm | 575 nm | 665 nm | 525 nm | 575 nm | 665 nm |
| 236 | 12 | 10 | 6 | 12 | 13 | 7 | 99 | 134 | 110 |
| 237 | 6 | 8 | 8 | 6 | 10 | 13 | 103 | 130 | 168 |
| 238 | 10 | 6 | 8 | 10 | 9 | 9 | 101 | 142 | 115 |
| 239 | 8 | 12 | 10 | 8 | 15 | 10 | 96 | 125 | 99 |

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A method for characterizing a fiber sample wherein the fiber sample comprises fibers,
   wherein the fibers comprise identification fibers,
   wherein the identification fibers comprise 1 to 100 chemical markers,
   wherein an amount of each of the chemical markers, based on a weight of the fibers, is defined as a chemical marker amount,
   wherein at least one of the chemical marker amounts corresponds to a taggant chemical marker amount, and
   wherein (i) the chemical markers and (ii) the at least one taggant chemical marker amounts are representative of at least one supply chain component of the fiber sample, and
   wherein the method comprises:
   (a) dissolving the fiber sample in a solvent to produce a sample solution and/or insolubles;
   (b) analyzing the sample solution and/or the insoluble to identify the chemical markers and each of the chemical marker amounts.

2. The method of claim 1, wherein the fibers further comprise standard fibers.

3. The method of claim 2, further comprising
   (a) correlating one or more of the chemical markers and the taggant chemical marker amounts to a database, wherein the database comprises manufacturer specific taggants; and
   (b) determining the at least one supply chain component of the fiber sample, wherein the at least one supply chain component comprises a manufacturer of the standard fibers, a manufacture site of the standard fibers, a manufacturing line of the standard fibers, a production run of the standard fibers, a production date of the standard fibers, a package of the standard fibers, a warehouse of the standard fibers, a customer of the standard fibers, a ship-to location of the standard fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, or a ship-to location of the fiber band.

4. The method of claim 3, wherein the at last one supply chain component comprises the manufacturer of the standard fibers or the fiber band comprising the fibers.

5. The method of claim 3, wherein the at last one supply chain component comprises the manufacturer of the standard fibers or the fiber band comprising the fibers and the customer of the standard fibers or the fiber band.

6. The method of claim 3, wherein the at last one supply chain component comprises the manufacturer of the standard fibers or a fiber band comprising the fibers and the ship-to location of the standard fibers or the fiber band.

7. The method of claim 3, wherein the fiber sample comprises a portion of a filter rod or a portion of a cigarette filter.

8. The method of claim 1, wherein the identification fibers comprise 1 to 50 of the chemical markers.

9. The method of claim 1, further comprising adding N,O-bis(trimethylsilyl)trifluoroacetamide to the sample solution.

10. The method of claim 1, wherein one or more of the chemical markers is selected from the group consisting of one or more taggant non-volatile organic compounds, one or more taggant photoluminescent materials, one or more taggant polymeric additives, one or more taggant carbohydrates, one or more taggant metal oxides, one or more taggant inorganic salts, one or more taggant optical isomers, one or more taggant isotopically labeled molecules, and one or more taggant trace chemicals inherent to a manufacturer of the standard fibers, and wherein a number of the taggant chemical marker amounts for each of the chemical makers ranges from 1 to 20.

11. The method of claim 10, wherein a number of the taggant nonvolatile organic compounds ranges from 1 to 20 and wherein the taggant non-volatile organic compounds comprise lauric acid, palmitic acid, or stearic acid.

12. The method of claim 10, wherein a number of the taggant photoluminescent materials ranges from 1 to 10, wherein the taggant photoluminescent materials comprise phosphorescent quantum dots, and wherein the phosphorescent quantum dots comprise Cd/Se ligand stabilized fluorescent nano-crystals.

13. The method of claim 10, wherein a number of the taggant polymeric additives ranges from 1 to 20, wherein the taggant polymeric additives comprise polystyrene, and wherein an average molecular weight of the polystyrene ranges from 500 to 20,000,000.

14. The method of claim 10, wherein a number of the taggant carbohydrates ranges from 1 to 10 and wherein the taggant carbohydrates comprise glucose, fructose, sucrose, or lactose.

15. The method of claim 10, wherein the chemical markers comprise the taggant metal oxides or the taggant inorganic salts,
wherein a number of the taggant metal oxides ranges from 1 to 20, or wherein a number of the taggant inorganic salts ranges from 1 to 20,
wherein the taggant metal oxides comprise titanium dioxide, zirconium oxides, zinc oxides, aluminum oxides, manganese oxides, magnesium oxides, calcium oxides, tin oxides, vanadium oxides, nickel oxides or iron oxide or wherein the taggant inorganic salts comprise salts of cesium, indium, or samarium.

16. The method of claim 1 and wherein each of the chemical marker amounts range from 100 ppb to 10,000 ppm, based on the weight of the fibers.

17. The method of claim 1, wherein the fibers comprise acrylic, modacrylic, aramid, nylon, polyester, polypropylene, rayon, polyacrylonitrile, polyethylene, PTFE, or cellulose acetate.

18. The method of claim 1, wherein the identification fibers comprise acrylic, modacrylic, aramid, nylon, polyester, polypropylene, rayon, polyacrylonitrile, polyethylene, PTFE, or cellulose acetate, and the standard fibers comprise cellulose acetate.

19. The method of claim 1, wherein the solvent comprises acetone, tetrahydrofuran, dichloromethane, methanol, chloroform, dioxane, N,N-dimethylformamide, dimethyl sulfoxide, methyl acetate, ethyl acetate, nitric acid or pyridine.

20. The method of claim 1, wherein the analyzing comprises a use of mass spectrometry, spectroscopy, nuclear magnetic resonance, or x-ray diffraction.

21. The method of claim 1, wherein the analyzing comprises a use of chromatography.

22. The method of claim 1, wherein the analyzing comprises a use of gas chromatography coupled to flame ionization detection, size exclusion chromatography followed by UV-vis spectroscopy, fluorescence spectroscopy, inductively coupled plasma (ICP) followed by mass spectrometry, or ICP followed by optical emission spectrometry.

23. The method of claim 1, further comprising
(a) correlating one or more of the chemical markers and the taggant chemical marker amounts to a database, wherein the database comprises manufacturer specific taggants; and
(b) determining the at least one supply chain component of the fiber sample, wherein the at least one supply chain component comprises a manufacturer of the fibers, a manufacture site of the fibers, a manufacturing line of the fibers, a production run of the fibers, a production date of the fibers, a package of the fibers, a warehouse of the fibers, a customer of the fibers, a ship-to location of the fibers, a manufacturer of a fiber band comprising the fibers, a manufacturing site of the fiber band, a manufacturing line of the fiber band, a production run of the fiber band, a production date of the fiber band, a package of the fiber band, a warehouse of the fiber band, a customer of the fiber band, or a ship-to location of the fiber band.

* * * * *